US012053345B2

(12) United States Patent
Tong et al.

(10) Patent No.: US 12,053,345 B2
(45) Date of Patent: Aug. 6, 2024

(54) METHOD OF ADMINISTERING ADHESIVE TO BOND ORTHODONTIC BRACKETS

(71) Applicant: Swift Health Systems Inc., Irvine, CA (US)

(72) Inventors: Hongsheng Tong, Yorba Linda, CA (US); Jichele Sanders, Chantilly, VA (US); Shermaine Dayot, Irvine, CA (US); Ishan Shinde, Santa Ana, CA (US)

(73) Assignee: Swift Health Systems Inc., Irvine, CA (US)

( * ) Notice: Subject to any disclaimer, the term of this patent is extended or adjusted under 35 U.S.C. 154(b) by 0 days.

(21) Appl. No.: 17/690,770

(22) Filed: Mar. 9, 2022

(65) Prior Publication Data
US 2023/0070165 A1 Mar. 9, 2023

Related U.S. Application Data

(60) Provisional application No. 63/240,627, filed on Sep. 3, 2021.

(51) Int. Cl.
*A61C 7/02* (2006.01)
*A61B 5/00* (2006.01)
(Continued)

(52) U.S. Cl.
CPC ............... *A61C 7/02* (2013.01); *A61B 5/0077* (2013.01); *A61C 7/002* (2013.01); *A61C 7/146* (2013.01); *A61C 7/16* (2013.01); *A61C 2202/01* (2013.01)

(58) Field of Classification Search
CPC .... A61C 7/02; A61C 7/08; A61C 7/10; A61C 7/12; A61C 7/146; A61C 7/16; A61C 2201/01; A61C 9/0053
See application file for complete search history.

(56) References Cited

U.S. PATENT DOCUMENTS 1,005,131 A 10/1911 Angle et al.
1,108,493 A 8/1914 Federspiel
(Continued)

FOREIGN PATENT DOCUMENTS

CN 1372872 10/2002
CN 201079455 7/2008
(Continued)

OTHER PUBLICATIONS

SinodentalGroup. Braces Bonding Teeth Gems Glue Light Cure Adhesive. Jun. 2021. https://sinodentalgroup.myshopify.com/products/sino-dental-group-orthodontic-brackets-glue-braces-bonding-light-cure-adhesive-kit?pr_prod_strat=use_description&pr_rec_id=0d0a6cdc9&pr_rec_pid=6687895355572&pr_ref_pid=6705886363.*

(Continued)

*Primary Examiner* — Heidi M Eide
*Assistant Examiner* — Lina Faraj
(74) *Attorney, Agent, or Firm* — Knobbe, Martens, Olson & Bear, LLP

(57) ABSTRACT

Methods of administering a quantity of adhesive to bond orthodontic brackets is disclosed herein. The quantity of adhesive to bond a selected bracket to a tooth at a specific location thereon can be calculated based on a known geometry of the selected bracket and a digital model of the patient's teeth. A instruction guide can visually indicate with a graphic the amount of adhesive to dispense from a syringe or other device to bond the selected bracket to the surface of the tooth at a specific location planned in the digital model.

11 Claims, 10 Drawing Sheets

(51) Int. Cl.
  *A61C 7/00* (2006.01)
  *A61C 7/14* (2006.01)
  *A61C 7/16* (2006.01)

(56) References Cited

U.S. PATENT DOCUMENTS

| | | | |
|---|---|---|---|
| 1,307,382 A | 6/1919 | Stanton |
| 1,323,141 A | 11/1919 | Young |
| 1,429,749 A | 9/1922 | Maeulen et al. |
| 1,638,006 A | 2/1926 | Aderer |
| 2,257,069 A | 9/1941 | Peak |
| 2,495,692 A | 1/1950 | Brusse |
| 2,524,763 A | 10/1950 | Brusse |
| 2,582,230 A | 1/1952 | Brusse |
| 3,256,602 A | 6/1966 | Broussard |
| 3,262,207 A | 7/1966 | Kesling |
| 3,374,542 A | 3/1968 | Moylan, Jr. |
| 3,464,113 A | 9/1969 | Silverman et al. |
| 3,593,421 A | 7/1971 | Brader |
| 3,600,808 A | 8/1971 | Reeve |
| 3,683,502 A | 8/1972 | Wallshein |
| 3,691,635 A | 9/1972 | Wallshein |
| 3,762,050 A | 10/1973 | Dal Pont |
| 3,765,091 A | 10/1973 | Northcutt |
| 3,878,610 A | 4/1975 | Coscina |
| 3,936,938 A | 2/1976 | Northcutt |
| 3,946,488 A | 3/1976 | Miller et al. |
| 3,949,477 A | 4/1976 | Cohen et al. |
| 3,975,823 A | 8/1976 | Sosnay |
| 4,103,423 A | 8/1978 | Kessel |
| 4,171,568 A | 10/1979 | Forster |
| 4,192,070 A | 3/1980 | Lemchen et al. |
| 4,193,195 A | 3/1980 | Merkel et al. |
| 4,197,643 A | 4/1980 | Burstone et al. |
| 4,268,250 A | 5/1981 | Reeve |
| 4,330,273 A | 5/1982 | Kesling |
| 4,354,833 A | 10/1982 | Fujita |
| 4,354,834 A | 10/1982 | Wilson |
| 4,382,781 A | 5/1983 | Grossman |
| 4,385,890 A | 5/1983 | Klein |
| 4,412,819 A | 11/1983 | Cannon |
| 4,424,033 A | 1/1984 | Wool |
| 4,436,510 A | 3/1984 | Klein |
| 4,479,779 A | 10/1984 | Wool |
| 4,483,674 A | 11/1984 | Schütz |
| 4,490,112 A | 12/1984 | Tanaka et al. |
| 4,501,554 A | 2/1985 | Hickham |
| 4,516,938 A | 5/1985 | Hall |
| 4,533,320 A | 8/1985 | Piekarsky |
| 4,561,844 A | 12/1985 | Bates |
| 4,580,976 A | 4/1986 | O'Meara |
| 4,582,487 A | 4/1986 | Creekmore |
| 4,585,414 A | 4/1986 | Kottermann |
| 4,592,725 A | 6/1986 | Goshgarian |
| 4,634,662 A | 1/1987 | Rosenberg |
| 4,656,860 A | 4/1987 | Orthuber et al. |
| 4,659,310 A | 4/1987 | Kottermann |
| 4,664,626 A | 5/1987 | Kesling |
| 4,674,978 A | 6/1987 | Acevedo |
| 4,676,747 A | 6/1987 | Kesling |
| 4,725,229 A | 2/1988 | Miller |
| 4,797,093 A | 1/1989 | Bergersen |
| 4,797,095 A | 1/1989 | Armstrong et al. |
| 4,838,787 A | 6/1989 | Lerner |
| 4,842,514 A | 6/1989 | Kesling |
| 4,872,449 A | 10/1989 | Beeuwkes |
| 4,881,896 A | 11/1989 | Bergersen |
| 4,892,479 A | 1/1990 | McKenna |
| 4,897,035 A | 1/1990 | Green |
| 4,900,251 A | 2/1990 | Andreasen |
| 4,978,323 A | 12/1990 | Freedman |
| 5,011,405 A | 4/1991 | Lemchen |
| 5,017,133 A | 5/1991 | Miura |
| 5,044,947 A | 9/1991 | Sachdeva et al. |
| 5,055,039 A | 10/1991 | Abbatte et al. |
| 5,092,768 A | 3/1992 | Korn |
| 5,114,339 A | 5/1992 | Guis |
| 5,123,838 A | 6/1992 | Cannon |
| 5,127,828 A | 7/1992 | Suyama |
| 5,131,843 A | 7/1992 | Hilgers et al. |
| 5,154,606 A | 10/1992 | Wildman |
| 5,174,754 A | 12/1992 | Meritt |
| 5,176,514 A | 1/1993 | Viazis |
| 5,176,618 A | 1/1993 | Freedman |
| 5,238,404 A | 8/1993 | Andreiko |
| 5,242,304 A | 9/1993 | Truax et al. |
| 5,248,257 A | 9/1993 | Cannon |
| 5,259,760 A | 11/1993 | Orikasa |
| 5,312,247 A | 5/1994 | Sachdeva et al. |
| 5,344,315 A | 9/1994 | Hanson |
| 5,368,478 A | 11/1994 | Andreiko |
| 5,380,197 A | 1/1995 | Hanson |
| 5,399,087 A | 3/1995 | Arndt |
| 5,431,562 A | 7/1995 | Andreiko |
| 5,447,432 A | 9/1995 | Andreiko |
| 5,454,717 A | 10/1995 | Andreiko |
| RE35,169 E | 3/1996 | Lemchen et al. |
| 5,516,284 A | 5/1996 | Wildman |
| 5,556,277 A | 9/1996 | Yawata et al. |
| 5,624,258 A | 4/1997 | Wool |
| 5,630,715 A | 5/1997 | Voudouris |
| 5,683,243 A | 11/1997 | Andreiko |
| 5,683,245 A | 11/1997 | Sachdeva et al. |
| 5,722,827 A | 3/1998 | Allesee |
| 5,727,941 A | 3/1998 | Kesling |
| 5,816,800 A | 10/1998 | Brehm |
| 5,820,370 A | 10/1998 | Brosius |
| 5,863,198 A | 1/1999 | Doyle |
| 5,890,893 A | 4/1999 | Heiser |
| 5,971,754 A | 10/1999 | Sondhi et al. |
| 5,975,893 A | 11/1999 | Chishti et al. |
| 5,993,208 A | 11/1999 | Jonjic |
| 6,015,289 A | 1/2000 | Andreiko |
| 6,036,489 A | 3/2000 | Brosius |
| 6,042,374 A | 3/2000 | Farzin-Nia et al. |
| 6,086,364 A | 7/2000 | Brunson |
| 6,089,861 A | 7/2000 | Kelly |
| 6,095,809 A | 8/2000 | Kelly et al. |
| 6,099,304 A | 8/2000 | Carter |
| 6,123,544 A | 9/2000 | Cleary |
| 6,183,250 B1 | 2/2001 | Kanno et al. |
| 6,190,166 B1 | 2/2001 | Sasakura |
| 6,196,839 B1 | 3/2001 | Ross |
| 6,213,767 B1 * | 4/2001 | Dixon .................. A61C 7/12 401/129 |
| 6,217,325 B1 | 4/2001 | Chishti et al. |
| 6,227,850 B1 | 5/2001 | Chishti et al. |
| 6,244,861 B1 | 6/2001 | Andreiko |
| 6,250,918 B1 | 6/2001 | Sachdeva et al. |
| 6,258,118 B1 | 7/2001 | Baum et al. |
| 6,315,553 B1 | 11/2001 | Sachdeva et al. |
| 6,318,994 B1 | 11/2001 | Chishti et al. |
| 6,318,995 B1 | 11/2001 | Sachdeva et al. |
| 6,334,853 B1 | 1/2002 | Kopelman et al. |
| 6,350,120 B1 | 2/2002 | Sachdeva et al. |
| 6,358,045 B1 | 3/2002 | Farzin-Nia et al. |
| 6,371,761 B1 | 4/2002 | Cheang et al. |
| 6,375,458 B1 | 4/2002 | Moorleghem et al. |
| 6,394,801 B2 | 5/2002 | Chishti et al. |
| 6,398,548 B1 | 6/2002 | Muhammad et al. |
| 6,413,084 B1 | 6/2002 | Rubbert et al. |
| 6,431,870 B1 | 8/2002 | Sachdeva |
| 6,450,807 B1 | 9/2002 | Chishti et al. |
| 6,464,495 B1 | 10/2002 | Voudouris |
| 6,464,496 B1 | 10/2002 | Sachdeva et al. |
| 6,471,511 B1 | 10/2002 | Chishti et al. |
| 6,471,512 B1 | 10/2002 | Sachdeva et al. |
| 6,512,994 B1 | 1/2003 | Sachdeva |
| 6,514,074 B1 | 2/2003 | Chishti et al. |
| 6,532,299 B1 | 3/2003 | Sachdeva et al. |
| 6,540,512 B1 | 4/2003 | Sachdeva et al. |
| 6,554,613 B1 | 4/2003 | Sachdeva et al. |
| 6,572,693 B1 | 6/2003 | Wu et al. |
| 6,582,226 B2 | 6/2003 | Jordan et al. |

(56) References Cited

U.S. PATENT DOCUMENTS

| | | |
|---|---|---|
| 6,587,828 B1 | 7/2003 | Sachdeva |
| 6,595,774 B1 | 7/2003 | Risse |
| 6,554,611 B2 | 8/2003 | Chishti et al. |
| 6,602,070 B2 | 8/2003 | Miller et al. |
| 6,612,143 B1 | 9/2003 | Butscher et al. |
| 6,616,444 B2 | 9/2003 | Andreiko |
| 6,626,666 B2 | 9/2003 | Chishti et al. |
| 6,629,840 B2 | 10/2003 | Chishti et al. |
| 6,632,089 B2 | 10/2003 | Rubbert |
| 6,648,640 B2 | 11/2003 | Rubbert |
| 6,663,385 B2 | 12/2003 | Tepper |
| 6,679,700 B2 | 1/2004 | McGann |
| 6,682,344 B1 | 1/2004 | Stockstill |
| 6,685,469 B2 | 2/2004 | Chishti et al. |
| 6,685,470 B2 | 2/2004 | Chishti et al. |
| 6,688,885 B1 | 2/2004 | Sachdeva et al. |
| 6,699,037 B2 | 3/2004 | Chishti et al. |
| 6,702,575 B2 | 3/2004 | Hilliard |
| 6,705,863 B2 | 3/2004 | Phan et al. |
| 6,722,878 B2 | 4/2004 | Graham |
| 6,722,880 B2 | 4/2004 | Chishti et al. |
| 6,728,423 B1 | 4/2004 | Rubbert et al. |
| 6,729,876 B2 | 5/2004 | Chishti et al. |
| 6,732,558 B2 | 5/2004 | Butscher et al. |
| 6,733,285 B2 | 5/2004 | Puttler et al. |
| 6,733,287 B2 | 5/2004 | Wilkerson |
| 6,733,288 B2 | 5/2004 | Vallittu et al. |
| 6,736,638 B1 | 5/2004 | Sachdeva et al. |
| 6,738,508 B1 | 5/2004 | Rubbert et al. |
| 6,739,869 B1 | 5/2004 | Taub et al. |
| 6,744,914 B1 | 6/2004 | Rubbert et al. |
| 6,744,932 B1 | 6/2004 | Rubbert et al. |
| 6,746,241 B2 | 6/2004 | Townsend-Hansen |
| 6,755,064 B2 | 6/2004 | Butscher |
| 6,771,809 B1 | 8/2004 | Rubbert et al. |
| 6,776,614 B2 | 8/2004 | Wiechmann |
| 6,830,450 B2 | 12/2004 | Knopp et al. |
| 6,845,175 B2 | 1/2005 | Kopelman et al. |
| 6,846,179 B2 | 1/2005 | Chapouland |
| 6,851,949 B1 | 2/2005 | Sachdeva et al. |
| 6,860,132 B2 | 3/2005 | Butscher |
| 6,893,257 B2 | 5/2005 | Kelly |
| 6,928,733 B2 | 8/2005 | Rubbert et al. |
| 6,948,931 B2 | 9/2005 | Chishti et al. |
| 6,960,079 B2 | 11/2005 | Brennan et al. |
| 6,971,873 B2 | 12/2005 | Sachdeva |
| 6,976,627 B1 | 12/2005 | Culp et al. |
| 6,988,889 B2 | 1/2006 | Abels |
| 7,008,221 B2 | 3/2006 | McGann |
| 7,013,191 B2 | 3/2006 | Rubbert |
| 7,020,963 B2 | 4/2006 | Cleary et al. |
| 7,029,275 B2 | 4/2006 | Rubbert |
| 7,033,171 B2 | 4/2006 | Wilkerson |
| 7,037,107 B2 | 5/2006 | Yamamoto |
| 7,056,115 B2 | 6/2006 | Phan et al. |
| 7,063,531 B2 | 6/2006 | Maijer et al. |
| 7,068,836 B1 | 6/2006 | Rubbert et al. |
| 7,076,980 B2 | 7/2006 | Butscher |
| 7,077,646 B2 | 7/2006 | Hilliard |
| 7,077,647 B2 | 7/2006 | Choi et al. |
| 7,080,979 B2 | 7/2006 | Rubbert et al. |
| 7,092,107 B2 | 8/2006 | Babayoff et al. |
| 7,094,053 B2 | 8/2006 | Andreiko |
| 7,112,065 B2 | 9/2006 | Kopelman et al. |
| 7,125,248 B2 | 10/2006 | Phan et al. |
| 7,134,874 B2 | 11/2006 | Chishti et al. |
| 7,137,812 B2 | 11/2006 | Cleary et al. |
| 7,155,373 B2 | 12/2006 | Jordan et al. |
| 7,156,661 B2 | 1/2007 | Choi et al. |
| 7,160,110 B2 | 1/2007 | Imgrund et al. |
| 7,168,950 B2 | 1/2007 | Cinader, Jr. et al. |
| 7,172,417 B2 | 2/2007 | Sporbert et al. |
| 7,175,428 B2 | 2/2007 | Nicholson |
| 7,186,115 B2 | 3/2007 | Goldberg et al. |
| 7,188,421 B2 | 3/2007 | Cleary et al. |
| 7,201,574 B1 | 4/2007 | Wiley |
| 7,204,690 B2 | 4/2007 | Hanson et al. |
| 7,214,056 B2 | 5/2007 | Stockstill |
| 7,229,282 B2 | 6/2007 | Andreiko |
| 7,234,934 B2 | 6/2007 | Rosenberg |
| 7,234,936 B2 | 6/2007 | Lai |
| 7,234,937 B2 | 6/2007 | Sachdeva et al. |
| 7,240,528 B2 | 7/2007 | Weise et al. |
| 7,244,121 B2 | 7/2007 | Brosius |
| 7,245,977 B1 | 7/2007 | Simkins |
| 7,252,506 B2 | 8/2007 | Lai |
| 7,267,545 B2 | 9/2007 | Oda |
| 7,283,891 B2 | 10/2007 | Butscher |
| 7,296,996 B2 | 11/2007 | Sachdeva |
| 7,335,021 B2 | 2/2008 | Nikodem |
| 7,347,688 B2 | 3/2008 | Kopelman et al. |
| 7,354,268 B2 | 4/2008 | Raby et al. |
| 7,357,634 B2 | 4/2008 | Knopp |
| 7,361,017 B2 | 4/2008 | Sachdeva |
| 7,364,428 B2 | 4/2008 | Cinader, Jr. et al. |
| 7,404,714 B2 | 7/2008 | Cleary et al. |
| 7,410,357 B2 | 8/2008 | Cleary et al. |
| 7,416,408 B2 | 8/2008 | Farzin-Nia et al. |
| 7,442,041 B2 | 10/2008 | Imgrund et al. |
| 7,452,205 B2 | 11/2008 | Cinader, Jr. et al. |
| 7,458,812 B2 | 12/2008 | Sporbert et al. |
| 7,469,783 B2 * | 12/2008 | Rose, Sr. ............... A61C 19/02 206/460 |
| 7,471,821 B2 | 12/2008 | Rubbert et al. |
| 7,473,097 B2 | 1/2009 | Raby et al. |
| 7,556,496 B2 | 7/2009 | Cinader, Jr. et al. |
| 7,578,673 B2 | 8/2009 | Wen et al. |
| 7,578,674 B2 | 8/2009 | Chishti et al. |
| 7,585,172 B2 | 9/2009 | Rubbert |
| 7,590,462 B2 | 9/2009 | Rubbert |
| 7,604,181 B2 | 10/2009 | Culp et al. |
| 7,621,743 B2 | 11/2009 | Bathen |
| 7,641,473 B2 | 1/2010 | Sporbert |
| 7,674,110 B2 | 3/2010 | Oda |
| 7,677,887 B2 | 3/2010 | Nicholson |
| 7,699,606 B2 | 4/2010 | Sachdeva et al. |
| 7,704,072 B2 | 4/2010 | Damon |
| 7,717,708 B2 | 5/2010 | Sachdeva |
| 7,722,354 B1 | 5/2010 | Dumas |
| 7,726,470 B2 | 6/2010 | Cinader, Jr. et al. |
| 7,726,968 B2 | 6/2010 | Raby et al. |
| 7,751,925 B2 | 7/2010 | Rubbert |
| 7,762,815 B2 | 7/2010 | Cinader, Jr. et al. |
| 7,811,087 B2 | 10/2010 | Wiechmann |
| 7,837,464 B2 | 11/2010 | Marshall |
| 7,837,466 B2 | 11/2010 | Griffith et al. |
| 7,837,467 B2 | 11/2010 | Butscher |
| 7,845,938 B2 | 12/2010 | Kim et al. |
| 7,850,451 B2 | 12/2010 | Wiechmann |
| 7,871,267 B2 | 1/2011 | Griffith et al. |
| 7,878,806 B2 | 2/2011 | Lemchen |
| 7,909,603 B2 | 3/2011 | Oda |
| D636,084 S | 4/2011 | Troester |
| D636,085 S | 4/2011 | Troester |
| 7,950,131 B2 | 5/2011 | Hilliard |
| 7,993,133 B2 | 8/2011 | Cinader, Jr. et al. |
| 8,021,146 B2 | 9/2011 | Cinader, Jr. et al. |
| 8,029,275 B2 | 10/2011 | Kesling |
| 8,033,824 B2 | 10/2011 | Oda et al. |
| 8,038,444 B2 | 10/2011 | Kitching et al. |
| 8,047,034 B2 | 11/2011 | Butscher |
| 8,057,226 B2 | 11/2011 | Wiechmann |
| 8,070,487 B2 | 12/2011 | Chishti et al. |
| 8,082,769 B2 | 12/2011 | Butscher |
| 8,092,215 B2 | 1/2012 | Stone-collonge et al. |
| 8,102,538 B2 | 1/2012 | Babayoff |
| 8,113,828 B1 | 2/2012 | Greenfield |
| 8,113,829 B2 | 2/2012 | Sachdeva |
| 8,114,327 B2 | 2/2012 | Cinader, Jr. et al. |
| 8,121,718 B2 | 2/2012 | Rubbert |
| 8,142,187 B2 | 3/2012 | Sporbert |
| 8,152,519 B1 | 4/2012 | Dumas et al. |
| 8,177,551 B2 * | 5/2012 | Sachdeva ............... A61C 9/0046 433/2 |

(56) References Cited

U.S. PATENT DOCUMENTS

| | | |
|---|---|---|
| 8,192,196 B2 | 6/2012 | Singh |
| 8,192,197 B2 | 6/2012 | Sporbert |
| 8,194,067 B2 | 6/2012 | Raby |
| 8,220,195 B2 | 7/2012 | Maijer et al. |
| 8,251,699 B2 | 8/2012 | Reising et al. |
| 8,266,940 B2 | 9/2012 | Riemeir et al. |
| 8,297,970 B2 | 10/2012 | Kanomi |
| 8,308,478 B2 | 11/2012 | Primus et al. |
| 8,313,327 B1 | 11/2012 | Won |
| 8,359,115 B2 | 1/2013 | Kopelman et al. |
| 8,363,228 B2 | 1/2013 | Babayoff |
| 8,366,440 B2 | 2/2013 | Bathen |
| 8,376,739 B2 | 2/2013 | Dupray |
| 8,382,917 B2 | 2/2013 | Johnson |
| 8,393,896 B2 | 3/2013 | Oda |
| 8,417,366 B2 | 4/2013 | Getto |
| 8,439,671 B2 | 5/2013 | Cinader, Jr. |
| 8,439,672 B2 | 5/2013 | Matov et al. |
| 8,451,456 B2 | 5/2013 | Babayoff |
| 8,454,364 B2 | 6/2013 | Taub et al. |
| 8,459,988 B2 | 6/2013 | Dumas |
| 8,465,279 B2 | 6/2013 | Bathen |
| 8,469,704 B2 | 6/2013 | Oda et al. |
| 8,479,393 B2 | 7/2013 | Abels et al. |
| 8,485,816 B2 | 7/2013 | Macchi |
| 8,491,306 B2 | 7/2013 | Raby et al. |
| D688,803 S | 8/2013 | Gilbert |
| 8,500,445 B2 | 8/2013 | Borri |
| 8,517,727 B2 | 8/2013 | Raby et al. |
| 8,545,221 B2 | 10/2013 | Sonte-collenge et al. |
| 8,550,814 B1 | 10/2013 | Collins |
| 8,562,337 B2 | 10/2013 | Kuo et al. |
| 8,573,972 B2 | 11/2013 | Matov et al. |
| 8,591,225 B2 | 11/2013 | Wu et al. |
| 8,591,226 B2 | 11/2013 | Griffith et al. |
| 8,636,505 B2 | 1/2014 | Fornoff |
| 8,638,447 B2 | 1/2014 | Babayoff et al. |
| 8,638,448 B2 | 1/2014 | Babayoff et al. |
| 8,675,207 B2 | 3/2014 | Babayoff |
| 8,678,818 B2 | 3/2014 | Dupray |
| 8,690,568 B2 | 4/2014 | Chapouland |
| 8,708,697 B2 | 4/2014 | Li et al. |
| 8,714,972 B2 | 5/2014 | Eichenberg |
| 8,734,149 B2 | 5/2014 | Phan et al. |
| 8,734,690 B2 | 5/2014 | Komori |
| 8,780,106 B2 | 7/2014 | Chishti et al. |
| 8,805,048 B2 | 8/2014 | Batesole |
| 8,805,563 B2 | 8/2014 | Kopelman et al. |
| 8,807,995 B2 | 8/2014 | Kabbani et al. |
| 8,827,697 B2 | 9/2014 | Cinader, Jr. et al. |
| 8,845,330 B2 | 9/2014 | Taub et al. |
| 8,871,132 B2 | 10/2014 | Abels et al. |
| 8,931,171 B2 | 1/2015 | Rosenberg |
| 8,932,054 B1 | 1/2015 | Rosenberg |
| 8,936,464 B2 | 1/2015 | Kopelman |
| 8,961,172 B2 | 2/2015 | Dupray |
| 8,968,365 B2 | 3/2015 | Aschmann et al. |
| 8,979,528 B2 | 3/2015 | Macchi |
| 8,986,004 B2 | 3/2015 | Dumas |
| 8,992,215 B2 | 3/2015 | Chapouland |
| 8,998,608 B2 | 4/2015 | Imgrund et al. |
| 9,022,781 B2 | 5/2015 | Kuo et al. |
| D731,659 S | 6/2015 | Singh |
| 9,066,775 B2 | 6/2015 | Bukhary |
| 9,089,386 B2 | 7/2015 | Hagelganz |
| D736,945 S | 8/2015 | Singh |
| 9,101,433 B2 | 8/2015 | Babayoff |
| 9,119,689 B2 | 9/2015 | Kabbani |
| 9,127,338 B2 | 9/2015 | Johnson |
| 9,144,473 B2 | 9/2015 | Aldo |
| 9,161,823 B2 | 10/2015 | Morton et al. |
| 9,204,942 B2 | 12/2015 | Phan et al. |
| 9,299,192 B2 | 3/2016 | Kopelman |
| 9,301,815 B2 | 4/2016 | Dumas |
| 9,329,675 B2 | 5/2016 | Ojelund et al. |
| 9,339,352 B2 | 5/2016 | Cinader et al. |
| 9,387,055 B2 | 7/2016 | Cinader, Jr. et al. |
| 9,402,695 B2 | 8/2016 | Curiel et al. |
| 9,427,291 B2 | 8/2016 | Khoshnevis et al. |
| 9,427,916 B2 | 8/2016 | Taub et al. |
| 9,433,477 B2 | 9/2016 | Borovinskih et al. |
| 9,439,737 B2 | 9/2016 | Gonzales et al. |
| 9,451,873 B1 | 9/2016 | Kopelman et al. |
| 9,492,246 B2 | 11/2016 | Lin |
| 9,498,302 B1 | 11/2016 | Patel |
| D774,193 S | 12/2016 | Makmel et al. |
| 9,510,757 B2 | 12/2016 | Kopelman et al. |
| 9,517,112 B2 | 12/2016 | Hagelganz et al. |
| 9,529,970 B2 | 12/2016 | Andreiko |
| 9,532,854 B2 | 1/2017 | Cinader et al. |
| 9,539,064 B2 | 1/2017 | Abels et al. |
| 9,554,875 B2 | 1/2017 | Gualano |
| 9,566,132 B2 | 2/2017 | Stone-collonge et al. |
| 9,566,134 B2 | 2/2017 | Hagelganz et al. |
| 9,585,733 B2 | 3/2017 | Voudouris |
| 9,585,734 B2 | 3/2017 | Lai et al. |
| 9,597,165 B2 | 3/2017 | Kopelman |
| 9,610,628 B2 | 4/2017 | Riemeier |
| 9,615,901 B2 | 4/2017 | Babayoff et al. |
| 9,622,834 B2 | 4/2017 | Chapouland |
| 9,622,835 B2 | 4/2017 | See et al. |
| 9,629,551 B2 | 4/2017 | Fisker et al. |
| 9,629,694 B2 | 4/2017 | Chun et al. |
| 9,642,678 B2 | 5/2017 | Kuo |
| 9,675,435 B2 | 6/2017 | Karazivan et al. |
| 9,707,056 B2 | 7/2017 | Machata et al. |
| 9,763,750 B2 | 9/2017 | Kim et al. |
| 9,788,917 B2 | 10/2017 | Mah |
| 9,814,543 B2 | 11/2017 | Huang et al. |
| 9,844,420 B2 | 12/2017 | Cheang |
| 9,848,958 B2 | 12/2017 | Matov et al. |
| 9,867,678 B2 | 1/2018 | Macchi |
| 9,867,680 B2 | 1/2018 | Damon |
| 9,872,741 B2 | 1/2018 | Gualano |
| 9,877,804 B2 | 1/2018 | Chester |
| 9,877,805 B2 | 1/2018 | Abels et al. |
| 9,925,020 B2 | 3/2018 | Jo |
| 9,937,018 B2 | 4/2018 | Martz et al. |
| 9,937,020 B2 | 4/2018 | Choi |
| 9,956,058 B2 | 5/2018 | Kopelman |
| 9,962,244 B2 | 5/2018 | Esbech et al. |
| 9,975,294 B2 | 5/2018 | Taub et al. |
| 9,987,105 B2 | 6/2018 | Dupray |
| 10,028,804 B2 | 7/2018 | Schulhof et al. |
| 10,045,834 B2 | 8/2018 | Gualano |
| 10,052,177 B2 | 8/2018 | Andreiko |
| 10,058,400 B2 | 8/2018 | Abels et al. |
| 10,058,401 B2 | 8/2018 | Tan |
| 10,064,706 B2 | 9/2018 | Dickerson |
| 10,070,943 B2 | 9/2018 | Fornoff |
| 10,076,780 B2 | 9/2018 | Riemeier et al. |
| 10,098,709 B1 | 10/2018 | Kitching et al. |
| 10,130,987 B2 | 11/2018 | Riemeier et al. |
| 10,136,966 B2 | 11/2018 | Reybrouck et al. |
| 10,149,738 B2 | 12/2018 | Lee |
| 10,179,035 B2 | 1/2019 | Shivapuja et al. |
| 10,179,036 B2 | 1/2019 | Lee |
| 10,219,877 B2 | 3/2019 | Khoshnevis et al. |
| 10,226,312 B2 | 3/2019 | Khoshnevis et al. |
| 10,238,476 B2 | 3/2019 | Karazivan et al. |
| 10,241,499 B1 | 3/2019 | Griffin |
| 10,278,791 B2 | 5/2019 | Schumacher |
| 10,278,792 B2 | 5/2019 | Wool |
| 10,278,793 B2 | 5/2019 | Gonzalez et al. |
| 10,292,789 B2 | 5/2019 | Martz et al. |
| 10,307,221 B2 | 6/2019 | Cinader, Jr. |
| 10,314,673 B2 | 6/2019 | Schulhof et al. |
| 10,327,867 B2 | 6/2019 | Nikolskiy et al. |
| 10,342,640 B2 | 7/2019 | Cassalia |
| 10,368,961 B2 | 8/2019 | Paehl et al. |
| 10,383,707 B2 | 8/2019 | Roein Peikar et al. |
| D859,663 S | 9/2019 | Cetta et al. |
| 10,413,386 B2 | 9/2019 | Moon et al. |
| 10,426,575 B1 | 10/2019 | Raslambekov |

(56) References Cited

U.S. PATENT DOCUMENTS

| | | |
|---|---|---|
| 10,456,228 B2 | 10/2019 | Karazivan et al. |
| 10,478,271 B2 | 11/2019 | Patel |
| 10,485,638 B2 | 11/2019 | Salah |
| 10,492,889 B2 | 12/2019 | Kim et al. |
| 10,492,890 B2 | 12/2019 | Cinader, Jr. et al. |
| 10,555,792 B2 | 2/2020 | Kopelman et al. |
| 10,588,717 B2 | 3/2020 | Chun et al. |
| 10,595,966 B2 | 3/2020 | Carrier, Jr. et al. |
| 10,603,137 B2 | 3/2020 | Alauddin et al. |
| 10,636,522 B2 | 4/2020 | Katzman et al. |
| 10,639,130 B2 | 5/2020 | Blees et al. |
| 10,639,134 B2 | 5/2020 | Shangjani et al. |
| 10,717,208 B1 | 7/2020 | Raslambekov et al. |
| 10,754,325 B1 | 8/2020 | Griffin, III |
| 10,758,323 B2 | 9/2020 | Kopelman |
| 10,772,706 B2 | 9/2020 | Schumacher |
| 10,806,376 B2 | 10/2020 | Lotan et al. |
| 10,809,697 B2 | 10/2020 | Grapsas |
| 10,828,133 B2 | 11/2020 | Tong et al. |
| 10,849,723 B1 | 12/2020 | Yancey et al. |
| 10,869,738 B2 | 12/2020 | Witte et al. |
| 10,881,488 B2 | 1/2021 | Kopelman |
| 10,881,489 B2 | 1/2021 | Tong et al. |
| 10,905,527 B2 | 2/2021 | Roein Peikar et al. |
| 10,932,887 B2 | 3/2021 | Hung |
| 10,935,958 B2 | 3/2021 | Sirovskiy et al. |
| 10,952,820 B2 | 3/2021 | Song et al. |
| 10,980,614 B2 | 4/2021 | Roein Peikar et al. |
| 10,984,549 B2 | 4/2021 | Goncharov et al. |
| 10,993,782 B1 | 5/2021 | Raslambekov |
| 10,993,785 B2 | 5/2021 | Roein Peikar et al. |
| 10,996,813 B2 | 5/2021 | Makarenkova et al. |
| 11,020,205 B2 | 6/2021 | Li et al. |
| 11,045,281 B2 | 6/2021 | Tsai et al. |
| 11,045,295 B2 | 6/2021 | Karazivan et al. |
| 11,058,517 B2 | 7/2021 | Tong et al. |
| 11,058,518 B2 | 7/2021 | Roein Peikar et al. |
| 11,058,520 B2 | 7/2021 | Khoshnevis et al. |
| 11,072,021 B2 | 7/2021 | Riemeier et al. |
| 11,083,411 B2 | 8/2021 | Yancey et al. |
| 11,083,546 B2 | 8/2021 | Cassalia |
| 11,103,330 B2 | 8/2021 | Webber et al. |
| 11,129,696 B2 | 9/2021 | Khoshnevis et al. |
| 11,147,652 B2 | 10/2021 | Mason et al. |
| 11,154,382 B2 | 10/2021 | Kopelman et al. |
| 11,229,505 B2 | 1/2022 | Schumacher et al. |
| 11,234,794 B2 | 2/2022 | Pokotilov et al. |
| 11,304,781 B2 | 4/2022 | Chun et al. |
| 11,317,994 B2 | 5/2022 | Peikar et al. |
| 11,317,995 B2 | 5/2022 | Peikar et al. |
| 11,324,572 B2 | 5/2022 | Peikar et al. |
| 11,331,165 B2 | 5/2022 | Owen |
| 11,337,486 B2 | 5/2022 | Oda et al. |
| 11,357,598 B2 | 6/2022 | Cramer |
| 11,382,720 B2 | 7/2022 | Kopelman et al. |
| 11,413,117 B2 | 8/2022 | Griffin, III et al. |
| 11,419,701 B2 | 8/2022 | Shanjani et al. |
| 11,433,658 B2 | 9/2022 | Friedrich et al. |
| 11,435,142 B2 | 9/2022 | Hauptmann |
| 11,446,117 B2 | 9/2022 | Paehl et al. |
| 11,446,219 B2 | 9/2022 | Kohler et al. |
| 11,464,604 B2 | 10/2022 | Makarenkova et al. |
| 11,471,254 B2 | 10/2022 | Owen |
| 11,471,255 B2 | 10/2022 | Cinader, Jr. et al. |
| 11,478,335 B2 | 10/2022 | Lai et al. |
| 11,478,337 B2 | 10/2022 | Griffin, III et al. |
| 11,490,995 B2 | 11/2022 | Wratten, Jr. et al. |
| 11,500,354 B2 | 11/2022 | Griffin, III et al. |
| 11,504,212 B2 | 11/2022 | Wratten, Jr. et al. |
| 11,510,757 B2 | 11/2022 | Khoshnevis et al. |
| 11,510,758 B2 | 11/2022 | Khoshnevis et al. |
| D972,732 S | 12/2022 | Villanueva |
| 11,517,405 B2 | 12/2022 | Khoshnevis et al. |
| 11,612,458 B1 | 3/2023 | Tong et al. |
| 11,612,459 B2 | 3/2023 | Tong et al. |
| 11,696,816 B2 | 7/2023 | Gardner |
| 2001/0055741 A1* | 12/2001 | Dixon .................... A61C 19/02 433/9 |
| 2002/0006597 A1 | 1/2002 | Andreiko et al. |
| 2002/0010568 A1 | 1/2002 | Rubbert et al. |
| 2002/0081546 A1 | 6/2002 | Tricca et al. |
| 2002/0098460 A1 | 7/2002 | Farzin-Nia |
| 2002/0192617 A1 | 12/2002 | Phan et al. |
| 2003/0049582 A1 | 3/2003 | Abels et al. |
| 2003/0070468 A1 | 4/2003 | Butscher et al. |
| 2003/0180689 A1 | 9/2003 | Arx et al. |
| 2003/0194677 A1 | 10/2003 | Sachdeva et al. |
| 2003/0207224 A1 | 11/2003 | Lotte |
| 2004/0048222 A1 | 3/2004 | Forster et al. |
| 2004/0072120 A1 | 4/2004 | Lauren |
| 2004/0083611 A1 | 5/2004 | Rubbert et al. |
| 2004/0166459 A1 | 8/2004 | Voudouris |
| 2004/0168752 A1 | 9/2004 | Julien |
| 2004/0199177 A1 | 10/2004 | Kim |
| 2004/0219471 A1 | 11/2004 | Cleary et al. |
| 2005/0043837 A1 | 2/2005 | Rubbert et al. |
| 2005/0074716 A1* | 4/2005 | Cleary .................... A61C 7/146 206/63.5 |
| 2005/0106529 A1 | 5/2005 | Abolfathi et al. |
| 2005/0181332 A1 | 8/2005 | Sernetz |
| 2005/0191592 A1 | 9/2005 | Farzin-Nia et al. |
| 2005/0233276 A1 | 10/2005 | Kopelman et al. |
| 2005/0244780 A1 | 11/2005 | Abels et al. |
| 2005/0244781 A1 | 11/2005 | Abels et al. |
| 2005/0244790 A1 | 11/2005 | Kuperman |
| 2006/0006092 A1* | 1/2006 | DuBos ................ B65D 73/0028 206/575 |
| 2006/0014116 A1 | 1/2006 | Maijer et al. |
| 2006/0068354 A1 | 3/2006 | Jeckel |
| 2006/0127834 A1 | 6/2006 | Szwajkowski et al. |
| 2006/0175209 A1* | 8/2006 | Sabilla .................... A61C 19/02 206/63.5 |
| 2006/0223021 A1 | 10/2006 | Cinader et al. |
| 2006/0223031 A1 | 10/2006 | Cinader, Jr. et al. |
| 2006/0257813 A1 | 11/2006 | Highland |
| 2006/0257821 A1 | 11/2006 | Cinader, Jr. et al. |
| 2007/0015103 A1 | 1/2007 | Sorel |
| 2007/0031773 A1 | 2/2007 | Scuzzo |
| 2007/0031775 A1 | 2/2007 | Andreiko |
| 2007/0087302 A1 | 4/2007 | Reising et al. |
| 2007/0107745 A1* | 5/2007 | Kiyomoto ................ A45D 31/00 132/73 |
| 2007/0111154 A1 | 5/2007 | Sampermans |
| 2007/0118215 A1 | 5/2007 | Moaddeb |
| 2007/0134611 A1 | 6/2007 | Nicholson |
| 2007/0134612 A1 | 6/2007 | Contencin |
| 2007/0141525 A1 | 6/2007 | Cinader, Jr. |
| 2007/0154859 A1 | 7/2007 | Hilliard |
| 2007/0172788 A1 | 7/2007 | Hill, II et al. |
| 2007/0190478 A1 | 8/2007 | Goldberg et al. |
| 2007/0231768 A1 | 10/2007 | Hutchinson |
| 2007/0235051 A1* | 10/2007 | Robinson ................ A45D 29/18 132/73.5 |
| 2007/0287121 A1 | 12/2007 | Cinader et al. |
| 2008/0032250 A1 | 2/2008 | Kopelman et al. |
| 2008/0057460 A1 | 3/2008 | Hicks |
| 2008/0063995 A1 | 3/2008 | Farzin-Nia et al. |
| 2008/0131831 A1 | 6/2008 | Abels et al. |
| 2008/0160475 A1 | 7/2008 | Rojas-Pardini |
| 2008/0199825 A1 | 8/2008 | Jahn |
| 2008/0227049 A1 | 9/2008 | Sevinc |
| 2008/0233528 A1 | 9/2008 | Kim et al. |
| 2008/0233530 A1 | 9/2008 | Cinader |
| 2008/0233531 A1 | 9/2008 | Raby et al. |
| 2008/0248439 A1 | 10/2008 | Griffith et al. |
| 2008/0254403 A1 | 10/2008 | Hilliard |
| 2008/0286711 A1 | 11/2008 | Corcoran et al. |
| 2008/0305450 A1 | 12/2008 | Steen |
| 2009/0004619 A1 | 1/2009 | Oda et al. |
| 2009/0019698 A1* | 1/2009 | Christoff ................ A61C 19/02 29/896.11 |
| 2009/0042160 A1 | 2/2009 | Ofir |
| 2009/0088838 A1 | 4/2009 | Shaolian et al. |
| 2009/0191502 A1 | 7/2009 | Cao et al. |

(56) References Cited

U.S. PATENT DOCUMENTS

| | | |
|---|---|---|
| 2009/0197217 A1 | 8/2009 | Butscher et al. |
| 2009/0216322 A1 | 8/2009 | Le et al. |
| 2009/0220907 A1 | 9/2009 | Suyama |
| 2009/0220920 A1 | 9/2009 | Primus et al. |
| 2009/0222075 A1 | 9/2009 | Gordon |
| 2010/0092903 A1 | 4/2010 | Sabilla |
| 2010/0092905 A1 | 4/2010 | Martin |
| 2010/0105000 A1 | 4/2010 | Scommegna et al. |
| 2010/0129765 A1 | 5/2010 | Mohr et al. |
| 2010/0129766 A1 | 5/2010 | Hilgers |
| 2010/0178628 A1 | 7/2010 | Kim |
| 2010/0179789 A1 | 7/2010 | Sachdeva et al. |
| 2010/0193979 A1 | 8/2010 | Goldberg et al. |
| 2010/0241120 A1 | 9/2010 | Bledsoe et al. |
| 2010/0279243 A1 | 11/2010 | Cinader, Jr. et al. |
| 2010/0304321 A1 | 12/2010 | Patel |
| 2011/0008745 A1 | 1/2011 | McQuillan et al. |
| 2011/0027743 A1 | 2/2011 | Cinader, Jr. et al. |
| 2011/0059414 A1 | 3/2011 | Hirsch |
| 2011/0091832 A1 | 4/2011 | Kim et al. |
| 2011/0220612 A1 | 9/2011 | Kim |
| 2011/0250556 A1 | 10/2011 | Heiser |
| 2011/0270583 A1 | 11/2011 | Getto et al. |
| 2011/0287376 A1 | 11/2011 | Walther |
| 2011/0314891 A1 | 12/2011 | Gilbert |
| 2012/0048432 A1 | 3/2012 | Johnson et al. |
| 2012/0148972 A1 | 6/2012 | Lewis |
| 2012/0208144 A1 | 8/2012 | Chiaramonte |
| 2012/0266419 A1 | 10/2012 | Browne et al. |
| 2012/0315595 A1 | 12/2012 | Beaudoin |
| 2012/0322019 A1 | 12/2012 | Lewis |
| 2013/0065193 A1 | 3/2013 | Curiel et al. |
| 2013/0122443 A1 | 5/2013 | Huang et al. |
| 2013/0177862 A1 | 7/2013 | Johnson |
| 2013/0196281 A1 | 8/2013 | Thornton |
| 2013/0196282 A1 | 8/2013 | Eichelberger et al. |
| 2013/0260329 A1 | 10/2013 | Voudouris |
| 2013/0315595 A1 | 11/2013 | Barr |
| 2014/0154637 A1 | 6/2014 | Hansen et al. |
| 2014/0170586 A1 | 6/2014 | Cantarella |
| 2014/0234794 A1 | 8/2014 | Vu |
| 2014/0255864 A1 | 9/2014 | Machata et al. |
| 2014/0287376 A1 | 9/2014 | Hultgren et al. |
| 2014/0363782 A1 | 12/2014 | Wiechmann et al. |
| 2015/0010879 A1 | 1/2015 | Kurthy |
| 2015/0064641 A1 | 3/2015 | Gardner |
| 2015/0072299 A1 | 3/2015 | Alauddin et al. |
| 2015/0140501 A1 | 5/2015 | Kim |
| 2015/0201943 A1 | 7/2015 | Brooks et al. |
| 2015/0265376 A1 | 9/2015 | Kopelman |
| 2015/0305833 A1 | 10/2015 | Cosse |
| 2015/0313687 A1 | 11/2015 | Blees et al. |
| 2015/0351872 A1 | 12/2015 | Jo |
| 2015/0359610 A1 | 12/2015 | Gonzalez et al. |
| 2015/0366638 A1 | 12/2015 | Kopelman et al. |
| 2016/0074139 A1 | 3/2016 | Machata et al. |
| 2016/0095670 A1 | 4/2016 | Witte et al. |
| 2016/0106522 A1 | 4/2016 | Kim |
| 2016/0135926 A1 | 5/2016 | Djamchidi |
| 2016/0166357 A1 | 6/2016 | Portalupi |
| 2016/0175073 A1 | 6/2016 | Huang |
| 2016/0206403 A1 | 7/2016 | Ouellette et al. |
| 2016/0228214 A1 | 8/2016 | Sachdeva et al. |
| 2016/0242871 A1 | 8/2016 | Morton et al. |
| 2016/0270885 A1 | 9/2016 | Kwon et al. |
| 2016/0278883 A1 | 9/2016 | Fasci et al. |
| 2016/0287354 A1 | 10/2016 | Viecilli et al. |
| 2016/0310239 A1 | 10/2016 | Paehl et al. |
| 2016/0374780 A1 | 12/2016 | Carrillo Gonzalez et al. |
| 2017/0086948 A1 | 3/2017 | Von Mandach |
| 2017/0105816 A1 | 4/2017 | Ward |
| 2017/0105817 A1 | 4/2017 | Chun et al. |
| 2017/0128169 A1 | 5/2017 | Lai et al. |
| 2017/0135793 A1 | 5/2017 | Webber et al. |
| 2017/0140381 A1* | 5/2017 | Ducrohet ............ H04L 63/0853 |
| 2017/0151037 A1 | 6/2017 | Lee |
| 2017/0156823 A1 | 6/2017 | Roein Peikar et al. |
| 2017/0165032 A1 | 6/2017 | Webber et al. |
| 2017/0165532 A1 | 6/2017 | Khan et al. |
| 2017/0181813 A1 | 6/2017 | Kalkhoran |
| 2017/0196660 A1 | 7/2017 | Lee |
| 2017/0224444 A1 | 8/2017 | Viecilli et al. |
| 2017/0231721 A1 | 8/2017 | Akeel et al. |
| 2017/0246682 A1 | 8/2017 | Duerig |
| 2017/0252140 A1 | 9/2017 | Murphy et al. |
| 2017/0281313 A1 | 10/2017 | Kim |
| 2017/0281314 A1 | 10/2017 | Freimuller |
| 2017/0296253 A1 | 10/2017 | Brandner et al. |
| 2017/0296304 A1 | 10/2017 | Tong et al. |
| 2017/0312052 A1* | 11/2017 | Moss .................... B33Y 80/00 |
| 2017/0318881 A1 | 11/2017 | Fonte et al. |
| 2017/0325911 A1 | 11/2017 | Marshall |
| 2017/0340777 A1 | 11/2017 | Ma et al. |
| 2018/0014915 A1 | 1/2018 | Voudouris |
| 2018/0014916 A1 | 1/2018 | Cinader, Jr. et al. |
| 2018/0021108 A1 | 1/2018 | Cinader, Jr. et al. |
| 2018/0049847 A1 | 2/2018 | Oda et al. |
| 2018/0055605 A1 | 3/2018 | Witte et al. |
| 2018/0071057 A1 | 3/2018 | Rudman |
| 2018/0110589 A1 | 4/2018 | Gao |
| 2018/0132974 A1 | 5/2018 | Rudman |
| 2018/0161121 A1 | 6/2018 | Butler et al. |
| 2018/0161126 A1 | 6/2018 | Marshall et al. |
| 2018/0168788 A1 | 6/2018 | Fernie |
| 2018/0185120 A1 | 7/2018 | Wool |
| 2018/0185121 A1 | 7/2018 | Pitts et al. |
| 2018/0206941 A1 | 7/2018 | Lee |
| 2018/0214250 A1 | 8/2018 | Martz |
| 2018/0235437 A1 | 8/2018 | Ozerov et al. |
| 2018/0243052 A1 | 8/2018 | Lee |
| 2018/0303583 A1* | 10/2018 | Tong .................... A61C 7/146 |
| 2018/0338564 A1 | 11/2018 | Oda et al. |
| 2019/0001396 A1 | 1/2019 | Riemeier et al. |
| 2019/0019187 A1 | 1/2019 | Miller et al. |
| 2019/0053876 A1 | 2/2019 | Sterental et al. |
| 2019/0090988 A1 | 3/2019 | Schumacher et al. |
| 2019/0090989 A1 | 3/2019 | Jo |
| 2019/0125494 A1 | 5/2019 | Li et al. |
| 2019/0142551 A1 | 5/2019 | Dickenson et al. |
| 2019/0159871 A1 | 5/2019 | Chan et al. |
| 2019/0163060 A1 | 5/2019 | Skamser et al. |
| 2019/0175304 A1 | 6/2019 | Morton et al. |
| 2019/0231488 A1 | 8/2019 | Dickerson |
| 2019/0247147 A1 | 8/2019 | Grande et al. |
| 2019/0252065 A1 | 8/2019 | Katzman et al. |
| 2019/0262103 A1 | 8/2019 | Cassalia |
| 2019/0276921 A1 | 9/2019 | Duerig et al. |
| 2019/0321136 A1 | 10/2019 | Martz et al. |
| 2019/0321138 A1 | 10/2019 | Roein Peikar et al. |
| 2019/0328487 A1 | 10/2019 | Levin et al. |
| 2019/0328491 A1 | 10/2019 | Hostettler et al. |
| 2019/0343606 A1 | 11/2019 | Wu et al. |
| 2019/0350682 A1 | 11/2019 | Cinader, Jr. et al. |
| 2019/0388189 A1 | 12/2019 | Shivapuja et al. |
| 2020/0000551 A1 | 1/2020 | Li et al. |
| 2020/0066391 A1 | 2/2020 | Sachdeva et al. |
| 2020/0107911 A1 | 4/2020 | Roein Peikar et al. |
| 2020/0129272 A1 | 4/2020 | Roein Peikar et al. |
| 2020/0138549 A1 | 5/2020 | Chun et al. |
| 2020/0146779 A1 | 5/2020 | Zhang |
| 2020/0146791 A1 | 5/2020 | Schülke et al. |
| 2020/0170757 A1 | 6/2020 | Kopelman et al. |
| 2020/0188063 A1 | 6/2020 | Cinader, Jr. et al. |
| 2020/0197131 A1 | 6/2020 | Matov et al. |
| 2020/0214806 A1 | 7/2020 | Hung |
| 2020/0229903 A1 | 7/2020 | Sandwick |
| 2020/0275996 A1 | 9/2020 | Tong et al. |
| 2020/0281611 A1 | 9/2020 | Kelly et al. |
| 2020/0338706 A1 | 10/2020 | Cunningham et al. |
| 2020/0345455 A1 | 11/2020 | Roein Peikar et al. |
| 2020/0345459 A1 | 11/2020 | Schueller et al. |
| 2020/0345460 A1 | 11/2020 | Roein Peikar et al. |
| 2020/0352765 A1 | 11/2020 | Lin |
| 2020/0360109 A1 | 11/2020 | Gao et al. |

(56) References Cited

U.S. PATENT DOCUMENTS

| | | | |
|---|---|---|---|
| 2020/0375270 A1 | 12/2020 | Holschuh et al. | |
| 2020/0375699 A1 | 12/2020 | Roein Peikar et al. | |
| 2020/0390524 A1 | 12/2020 | Roein Peikar et al. | |
| 2020/0405191 A1 | 12/2020 | Lotan et al. | |
| 2020/0405452 A1 | 12/2020 | Song et al. | |
| 2021/0007830 A1 | 1/2021 | Roein Peikar et al. | |
| 2021/0007832 A1 | 1/2021 | Roein Peikar et al. | |
| 2021/0045701 A1 | 2/2021 | Unklesbay et al. | |
| 2021/0068928 A1 | 3/2021 | Witte et al. | |
| 2021/0077227 A1 | 3/2021 | Griffin, III et al. | |
| 2021/0093422 A1 | 4/2021 | Tong et al. | |
| 2021/0128275 A1 | 5/2021 | Suh et al. | |
| 2021/0134450 A1 | 5/2021 | Katzman et al. | |
| 2021/0137644 A1 | 5/2021 | Benarouch et al. | |
| 2021/0145547 A1 | 5/2021 | Roein Peikar et al. | |
| 2021/0177551 A1 | 6/2021 | Roein Peikar et al. | |
| 2021/0186662 A1 | 6/2021 | Roein Peikar et al. | |
| 2021/0205049 A1 | 7/2021 | Cinader, Jr. | |
| 2021/0212803 A1 | 7/2021 | Tong et al. | |
| 2021/0244502 A1 | 8/2021 | Farkash et al. | |
| 2021/0244505 A1 | 8/2021 | Tong et al. | |
| 2021/0244507 A1 | 8/2021 | Curiel et al. | |
| 2021/0251730 A1 | 8/2021 | Curiel et al. | |
| 2021/0259808 A1 | 8/2021 | Ben-gal Nguyen et al. | |
| 2021/0275286 A1 | 9/2021 | Karazivan et al. | |
| 2021/0330430 A1 | 10/2021 | Khoshnevis et al. | |
| 2021/0338380 A1 | 11/2021 | Park et al. | |
| 2021/0346127 A1 | 11/2021 | Cassalia | |
| 2021/0353389 A1 | 11/2021 | Peikar et al. | |
| 2021/0369413 A1 | 12/2021 | Li et al. | |
| 2021/0378792 A1 | 12/2021 | Akopov et al. | |
| 2021/0386523 A1 | 12/2021 | Raby, II et al. | |
| 2021/0393375 A1 | 12/2021 | Chekh et al. | |
| 2021/0401546 A1 | 12/2021 | Gardner | |
| 2021/0401548 A1 | 12/2021 | Oda et al. | |
| 2022/0008169 A1 | 1/2022 | Reisman | |
| 2022/0023009 A1 | 1/2022 | Tong et al. | |
| 2022/0031428 A1 | 2/2022 | Khoshnevis et al. | |
| 2022/0039921 A1 | 2/2022 | Kopelman et al. | |
| 2022/0039922 A1 | 2/2022 | Yamaguchi | |
| 2022/0061964 A1 | 3/2022 | Khoshnevis et al. | |
| 2022/0087783 A1 | 3/2022 | Khoshnevis et al. | |
| 2022/0133438 A1 | 5/2022 | Wratten, Jr. et al. | |
| 2022/0137592 A1 | 5/2022 | Cramer et al. | |
| 2022/0168072 A1 | 6/2022 | Tong et al. | |
| 2022/0183797 A1 | 6/2022 | Khoshnevis et al. | |
| 2022/0226076 A1 | 7/2022 | Roein Peikar et al. | |
| 2022/0226077 A1 | 7/2022 | Roein Peikar et al. | |
| 2022/0249201 A1 | 8/2022 | Shuman et al. | |
| 2022/0257341 A1 | 8/2022 | Somasundaram et al. | |
| 2022/0257344 A1 | 8/2022 | Tsai et al. | |
| 2022/0287804 A1 | 9/2022 | Oda | |
| 2022/0304773 A1 | 9/2022 | Wratten, Jr. et al. | |
| 2022/0304774 A1 | 9/2022 | Wratten, Jr. et al. | |
| 2022/0314508 A1 | 10/2022 | Subramaniam et al. | |
| 2022/0323183 A1 | 10/2022 | Dufour et al. | |
| 2022/0338960 A1 | 10/2022 | Reising | |
| 2022/0346912 A1 | 11/2022 | Li et al. | |
| 2022/0361996 A1 | 11/2022 | Raby et al. | |
| 2023/0070837 A1 | 3/2023 | Oda | |
| 2023/0072074 A1 | 3/2023 | Oda | |
| 2023/0100466 A1 | 3/2023 | Huynh et al. | |

FOREIGN PATENT DOCUMENTS

| | | | |
|---|---|---|---|
| CN | 201320224 Y | 10/2009 | |
| CN | 102215773 | 10/2011 | |
| CN | 202365955 | 8/2012 | |
| CN | 202892116 | 4/2013 | |
| CN | 203074896 | 7/2013 | |
| CN | 103505293 | 1/2014 | |
| CN | 203506900 | 4/2014 | |
| CN | 104188728 | 12/2014 | |
| CN | 204049881 | 12/2014 | |
| CN | 205126459 | 4/2016 | |
| CN | 105596098 | 5/2016 | |
| CN | 105662615 | 6/2016 | |
| CN | 205569100 | 9/2016 | |
| CN | 106029002 | 10/2016 | |
| CN | 106137419 | 11/2016 | |
| CN | 108690967 | 10/2018 | |
| CN | 109009504 | 12/2018 | |
| DE | 3915807 | 11/1990 | |
| DE | 20 2018 003 574 U1 | 8/2018 | |
| DE | 10 2018 005 769 A1 | 1/2020 | |
| DE | 10 2018 133 705 A1 | 7/2020 | |
| DE | 10 2015 017 301 B3 | 3/2022 | |
| EP | 0 778 008 | 6/1997 | |
| EP | 1 139 902 | 10/2001 | |
| EP | 1 276 433 | 1/2003 | |
| EP | 1 379 193 B1 | 2/2007 | |
| EP | 2 076 207 | 7/2009 | |
| EP | 1 073 378 B1 | 1/2012 | |
| EP | 2 522 298 | 11/2012 | |
| EP | 2 617 383 | 7/2013 | |
| EP | 3 285 678 | 5/2021 | |
| EP | 3 954 320 | 2/2022 | |
| EP | 2 726 049 | 8/2022 | |
| EP | 3 019 141 | 8/2022 | |
| EP | 4 034 077 | 8/2022 | |
| EP | 4 035 649 | 8/2022 | |
| EP | 4 044 959 | 8/2022 | |
| EP | 4 048 196 | 8/2022 | |
| EP | 4065647 A1 | 8/2022 | |
| EP | 3 691 559 | 9/2022 | |
| EP | 3 823 813 | 9/2022 | |
| EP | 3 905 986 | 9/2022 | |
| EP | 4 056 144 | 9/2022 | |
| ES | 2315046 | 4/2010 | |
| FR | 2 525 469 | 10/1983 | |
| FR | 3 056 393 B1 | 10/2018 | |
| JP | 11221235 A | 8/1999 | |
| JP | 2009205330 A | 9/2009 | |
| KR | 100549294 | 2/2006 | |
| KR | 100737442 | 7/2007 | |
| KR | 100925286 | 11/2009 | |
| KR | 101301886 | 8/2013 | |
| KR | 101583547 | 1/2016 | |
| KR | 101584737 | 1/2016 | |
| KR | 101723674 | 4/2017 | |
| RU | 133408 U1 | 10/2013 | |
| WO | WO 01/80761 | 11/2001 | |
| WO | WO 01/85047 | 11/2001 | |
| WO | WO 2003/045266 | 6/2003 | |
| WO | WO 2005/008441 | 1/2005 | |
| WO | WO 2005/094716 | 10/2005 | |
| WO | WO 2007/069286 | 6/2007 | |
| WO | WO 2008/051774 | 5/2008 | |
| WO | WO 2011/034522 | 3/2011 | |
| WO | WO 2011/090502 | 7/2011 | |
| WO | WO 2011/103669 | 9/2011 | |
| WO | WO 2012/089735 | 7/2012 | |
| WO | WO 2012/140021 | 10/2012 | |
| WO | WO 2013/019398 | 2/2013 | |
| WO | WO 2014/070920 | 5/2014 | |
| WO | WO 2016/148961 | 9/2016 | |
| WO | WO 2016/149008 | 9/2016 | |
| WO | WO 2016/199972 | 12/2016 | |
| WO | WO 2016/210402 | 12/2016 | |
| WO | WO 2017/007079 | 1/2017 | |
| WO | WO 2017/112004 | 6/2017 | |
| WO | WO 2017/172537 | 10/2017 | |
| WO | WO 2017/184632 | 10/2017 | |
| WO | WO 2017/194478 | 11/2017 | |
| WO | WO 2017/198640 | 11/2017 | |
| WO | WO 2018/102588 | 6/2018 | |
| WO | WO 2018/122862 | 7/2018 | |
| WO | WO 2018/144634 | 8/2018 | |
| WO | WO 2018/195356 | 10/2018 | |
| WO | WO 2019/135504 | 7/2019 | |
| WO | WO 2020/095182 | 5/2020 | |
| WO | WO 2020/178353 | 9/2020 | |
| WO | WO 2020/180740 | 9/2020 | |
| WO | WO 2020/223744 | 11/2020 | |

(56) References Cited

FOREIGN PATENT DOCUMENTS

| | | |
|---|---|---|
| WO | WO 2020/223745 | 11/2020 |
| WO | WO 2021/087158 | 5/2021 |
| WO | WO 2021/105878 | 6/2021 |
| WO | WO 2021/214613 | 10/2021 |
| WO | WO 2021/225916 A2 | 11/2021 |
| WO | WO 2021/226618 | 11/2021 |
| WO | WO 2021/225916 A3 | 12/2021 |
| WO | WO 2021/245484 | 12/2021 |
| WO | WO 2021/252675 | 12/2021 |
| WO | WO 2022/099263 | 5/2022 |
| WO | WO 2022/099267 | 5/2022 |
| WO | WO 2022/123402 | 6/2022 |
| WO | WO 2022/137109 | 6/2022 |
| WO | WO 2022/145602 | 7/2022 |
| WO | WO 2022/159738 | 7/2022 |
| WO | WO 2022/162488 | 8/2022 |
| WO | WO 2022/162528 | 8/2022 |
| WO | WO 2022/162614 | 8/2022 |
| WO | WO 2022/167899 | 8/2022 |
| WO | WO 2022/167995 | 8/2022 |
| WO | WO 2022/180466 | 9/2022 |
| WO | WO 2022/189906 | 9/2022 |
| WO | WO 2022/192409 | 9/2022 |
| WO | WO 2022/195391 | 9/2022 |
| WO | WO 2022/204711 | 9/2022 |
| WO | WO 2022/214895 | 10/2022 |
| WO | WO 2022/217269 | 10/2022 |
| WO | WO 2022/219459 | 10/2022 |
| WO | WO 2022/229734 | 11/2022 |
| WO | WO 2022/229739 | 11/2022 |
| WO | WO 2022/236287 | 11/2022 |
| WO | WO-2022236027 A1 * | 11/2022 |
| WO | WO 2023/033869 | 3/2023 |
| WO | WO 2023/033870 | 3/2023 |
| WO | WO 2023/034876 | 3/2023 |

OTHER PUBLICATIONS

Coro, Jorge C. et al., "MEAW Therapy" MEAW Therapy—Orthodontic Products, accessed via http://www.orthodonticproductsonline.com/2012/11/meaw-therapy/ on Mar. 14, 2016, published Nov. 12, 2012 in 6 pages.

ElSheikh, Moaaz Mohamed, et al. "A Forsus Distalizer: A Pilot Typodont Study". Jul.-Dec. 2004, KDJ, vol. 7, No. 2, pp. 107-115.

Gilbert, Alfredo. An in-office wire-bending robot for lingual orthodontics. ResearchGate. Article in Journal of clinical orthodontics: JCO, Apr. 2011.

Glauser-Williams Orthodontics: Appliances, http://www.glauserwilliamsorthodontics.com/treatments/orthodontic-appliances.php , accessed Nov. 30, 2015 in 4 pages.

Jiang et al. Bending Process Analysis and Structure Design of Orthodontic Archwire Bending Robot. International Journal of Smart Home. vol. 7, No. 5 (2013), pp. 345-352. http://dx.doi.org/10.14257/ijsh.2013.7.5.33.

Jiang et al. A Review on Robot in Prosthodontics and Orthodontics. Hindawi Publishing Corporation. Advances in Mechanical Engineering. Article ID 198748. 2014. 11 pages.

Mahony, Derek, "How We Got From There to Here and Back". Dental Learning Hub (Capture of web page dated Jun. 24, 2013 downloaded from http://web.archive.org/web/20130624145806/http://www.dental-learninghub.com/Clinical/Orthodontics.aspx, downloaded Feb. 7, 2014).

Miller, R.J. et al. "Validation of Align Technology's Treat III™ Digital Model Superimposition Tool and Its Case Application". Orthodontic Craniofacial Res.,2003, vol. 6 (Suppl 1): pp. 143-149.

SureSmile. 2013. About SureSmile. (Capture of web page dated Jun. 21, 2013 downloaded from http://web.archive.org/web/20130621031404/http://suresmile.com/About-SureSmile, downloaded Feb. 7, 2014).

Xia, et al. Development of a Robotic System for Orthodontic Archwire Bending. 2016 IEEE International Conference on Robotics and Automation (ICRA). Stockholm, Sweden, May 16-21, 2016. pp. 730-735.

Yang, Won-Sik, et al. "A Study of the Regional Load Deflection Rate of Multiloop Edgewise Arch Wire." Angle Orthodontist, 2001, vol. 7, No. 2, pp. 103-109.

IPhone 3D scanning to dental software, screen shots at 0:09 and 7:00 of YouTube video, https://www.youtube.com/watch?v=QONGdQ3QiFE, uploaded Oct. 1, 2018 in 2 pages.

Invisalign® SmileView™, How Would You Look with Straight Teeth?, https://www.invisalign.com/get-started/invisalign-smileview?v=0#start, printed Jun. 7, 2022 in 2 pages.

A ScanBox demo, https://www.youtube.com/watch?v=MsCfv2PDQ0o, screen shots at 0:08 and 0:19 of YouTube video, uploaded May 5, 2019 in 2 pages.

Southern Maine Orthodontics, Virtual Orthodontic Treatment, https://southernmainebraces.com/virtual-orthodontic-treatment/, printed Jun. 7, 2022 in 3 pages.

International Search Report and Written Opinion in Application No. PCT/US2022/019626, mailed May 23, 2022, in 14 pages.

Spini et al., "Transition temperature range of thermally activated nickel-titanium archwires", J Appl Oral Sci., dated Apr. 2014, vol. 22, No. 2, pp. 109-117.

In Brace, Brush & Floss Easily with In Brace, dated as uploaded on: May 26, 2022, YouTube, Retrieved from Internet: https://www.youtube.com/watch?v=uAsxiBlbY4Y (Dated Year: 2022).

MEAW School, Introduction to MEAW (Multi-loop Edgewise Arch Wire), dated as uploaded On: Mar. 24, 2021, YouTube, Retrieved from Internet: https://www.youtube.com/watch?v=ne785jlzN_Pg (Year: 2021).

Richard Gawel, Swift Health Systems Raises $45 Million to Finance Invisible Orthodontics, dated as published on: Dec. 4, 2019, dentistrytoday.com, Retrieved from Internet: https://www.dentistrytoday.com/products/swift-health-systems-raises-45-million-to-finance-invisible-orthodontics/ (Dated Year: 2019).

In Brace, What Is In Brace?—Integration Booster, dated as uploaded on: May 22, 2023, YouTube, Retrieved from Internet: https://www.youtube.com/watch?v=ANUPkCSfQo4 (Dated Year: 2023).

* cited by examiner

700

Method of Determining A quantity of Adhesive to Bond a Bracket to a Tooth Surface

702
Scan inside of patient's mouth

704
Create digital model of patient's teeth

706
Select a digital bracket to be placed on a tooth of the digital model

708
Digitally position the digital bracket on a surface of the tooth of digital model 710
Determine quantity of adhesive to bond a contact surface of a bracket corresponding to the digital bracket to a respective surface of a tooth corresponding to the tooth of the digital model based at least partially on the known geometry of the contact surface of the bracket and the geometry of the surface of the tooth

Method of Applying a Quantity of adhesive to Brackets for Bonding

902 — Load IDB tray with brackets

904 — Dispense adhesive from syringe to match a size of an adhesive quantity graphic on a fill guide 906 — Cut dispensed adhesive from syringe tip 908 — Transfer dispensed adhesive to the contact surface of a respective bracket 910 — Distribute adhesive over the contact surface 912 — Store IDB tray with adhesive applied to brackets in light-proof case

FIG. 10

METHOD OF ADMINISTERING ADHESIVE TO BOND ORTHODONTIC BRACKETS

CROSS REFERENCE TO RELATED APPLICATIONS

This application claims priority to U.S. Provisional Patent Application No. 63/240,627, filed Sep. 3, 2021, which is incorporated herein by reference in its entirety. Any and all applications, if any, for which a foreign or domestic priority claim is identified in the Application Data Sheet of the present application is hereby incorporated by reference under 37 CFR 1.57.

BACKGROUND

Field

The present disclosure relates in some aspects to methods of administering adhesive to bond orthodontic brackets to a patient's teeth.

SUMMARY

It can be difficult to determine a quantity of adhesive that is suitable for bonding an orthodontic bracket to a patient's tooth. If too much adhesive is used, a clinician may need to clean up excess adhesive post bonding, which can waste adhesive and extend the length of a patient's chair time. If too little adhesive is used, a weak bond may be formed between the orthodontic bracket and the patient's tooth, which may result in the orthodontic bracket inadvertently debonding from the tooth. Accordingly, methods, systems, and apparatuses are disclosed herein which determine and/or administer a quantity of adhesive for bonding an orthotic bracket to a patient's tooth.

In some variants, a method of determining a quantity of adhesive to bond an orthodontic bracket to a tooth surface is disclosed herein. The method can include scanning an inside of a mouth of a patient. The method can include creating a digital model of teeth of the patient. The method can include selecting a digital bracket to be placed on a digital tooth of the digital model. The digital bracket having a bonding surface with a known geometry. The method can include positioning the digital bracket at a location on a surface of the digital tooth of the digital model. The method can include determining a quantity of adhesive to bond a bonding surface of a physical orthodontic bracket, corresponding to the bonding surface of the digital bracket, to a location of a surface of a physical tooth, corresponding to the location of the surface of the digital tooth, based at least partially on the known geometry of the bonding surface of the digital bracket and a geometry at the location of the surface of the digital tooth where the digital bracket is positioned.

In some variants, scanning the inside of the mouth of the patient is performed using a mobile device.

In some variants, scanning the inside of the mouth of the patient can include 3D scanning.

In some variants, scanning the inside of the mouth of the patient can include taking 2D images.

In some variants, selecting the digital bracket can include selecting the digital bracket from a plurality of digital brackets having unique characteristics.

In some variants, the digital bracket can be automatically selected based on one or more characteristics of the digital tooth.

In some variants, selecting the digital bracket can include selecting the digital bracket from a plurality of suggested digital brackets.

In some variants, the digital bonding surface and corresponding physical bonding surface can include one or more contours to facilitate improved bonding.

In some variants, the quantity of adhesive to bond the bonding surface of the physical orthodontic bracket to the location of the surface of the physical tooth can be determined by an algorithm.

In some variants, a method of determining a quantity of adhesive to be applied to an orthodontic bracket for bonding is disclosed herein. The method can include dispensing an adhesive from a container. The method can include visually comparing a size of a profile of the dispensed adhesive with an adhesive quantity graphic on an instructional guide. The method can include discontinuing the dispensing of the adhesive from the container when the profile of the dispensed adhesive matches the adhesive quantity graphic on the instructional guide.

In some variants, the method can include transferring the dispensed adhesive to a bonding surface of an orthodontic bracket.

In some variants, the method can include distributing the dispensed adhesive over the contact surface of the orthodontic bracket.

In some variants, distributing the dispensed adhesive over the contact surface of the orthodontic bracket can include using a microbrush.

In some variants, the method can include loading a well of an indirect bonding tray (IDB) tray with the orthodontic bracket.

In some variants, the method can include storing the loaded IDB tray in a light-proof case to prevent the adhesive from curing.

In some variants, the method can include placing the IDB tray on the teeth of the patient to position the orthodontic bracket at a preplanned position on a tooth.

In some variants, the method can include exposing the adhesive to UV light to cure the adhesive.

In some variants, a width of an opening of the container and a width of the adhesive quantity graphic can be the same such that visually comparing the size of the profile of the dispensed adhesive with the adhesive quantity graphic on the instructional guide includes comparing a length of the profile of the dispensed adhesive with a length of the adhesive quantity graphic.

In some variants, the container can be a syringe.

In some variants, the method can include cutting the dispensed adhesive from an end of the container.

In some variants, cutting the dispensed adhesive from the end of the container can include cutting with a composite instrument. The composite instrument can be thin.

In some variants, a kit is disclosed herein. The kit can include a container that can have a cavity that can to hold an adhesive therein. The kit can include an instructional guide that can include an adhesive quantity graphic. The adhesive quantity graphic can be visually compared with a profile of adhesive dispensed from the container to determine a quantity of dispensed adhesive to be applied to an orthodontic bracket for bonding on a location of a tooth of a patient.

In some variants, the container can be a syringe.

In some variants, the cavity can hold the adhesive therein.

In some variants, the kit can include a second container that can house the adhesive to be transferred to the cavity of the container for dispensing.

In some variants, the container can include an opening through which adhesive housed in the cavity can be dispensed.

In some variants, the opening of the container can have a width that is the same as a width of the adhesive quantity graphic such that a length of the profile of adhesive dispensed from the container can be visually compared with a length of the adhesive quantity graphic to determine the quantity of dispensed adhesive to be applied to the orthodontic bracket for bonding.

In some variants, the instructional guide can include a plurality of adhesive quantity graphics and a plurality of tooth identifiers corresponding to respective teeth of a patient. Each of the plurality of adhesive quantity graphics can be, respectively, juxtaposed one of the plurality of tooth identifiers to visually indicate the quantity of dispensed adhesive to be applied to the orthodontic bracket corresponding to the tooth identifier.

In some variants, the kit can include an instrument to cut the dispensed adhesive from the container.

In some variants, the instrument is a composite instrument. The composite instrument can be thin.

In some variants, the kit can include a microbrush to distribute the dispensed adhesive over a contact surface of the orthodontic bracket.

In some variants, the kit can include an indirect bonding tray (IDB) tray.

In some variants, the kit can include a light-proof case that can to delay or prevent curing of the adhesive.

In some variants, the instructional guide can include patient identifying information.

In some variants, the kit can include adhesive.

In some variants, the kit can include one or more archforms.

In some variants, the one or more archforms can be made of a shape memory material and set in a custom nonplanar shape that can move teeth of a patient.

In some variants, the can include a plurality of orthodontic brackets.

In some variants, the plurality of orthodontic brackets can be loaded in an indirect bonding (IDB) tray.

In some variants, the adhesive quantity graphic can be printed on the instructional guide.

BRIEF DESCRIPTION OF THE DRAWINGS

These drawings are illustrative embodiments and do not present all possible embodiments of this invention. The illustrated embodiments are intended to illustrate, but not to limit, the scope of protection. Various features of the different disclosed embodiments can be combined to form further embodiments, which are part of this disclosure.

FIG. 7 illustrates a method of determining a quantity of adhesive to bond an orthodontic bracket to a tooth surface.

FIG. 10 illustrates a method of applying a quantity of adhesive to orthodontic brackets for bonding.

DETAILED DESCRIPTION

Figure 1:
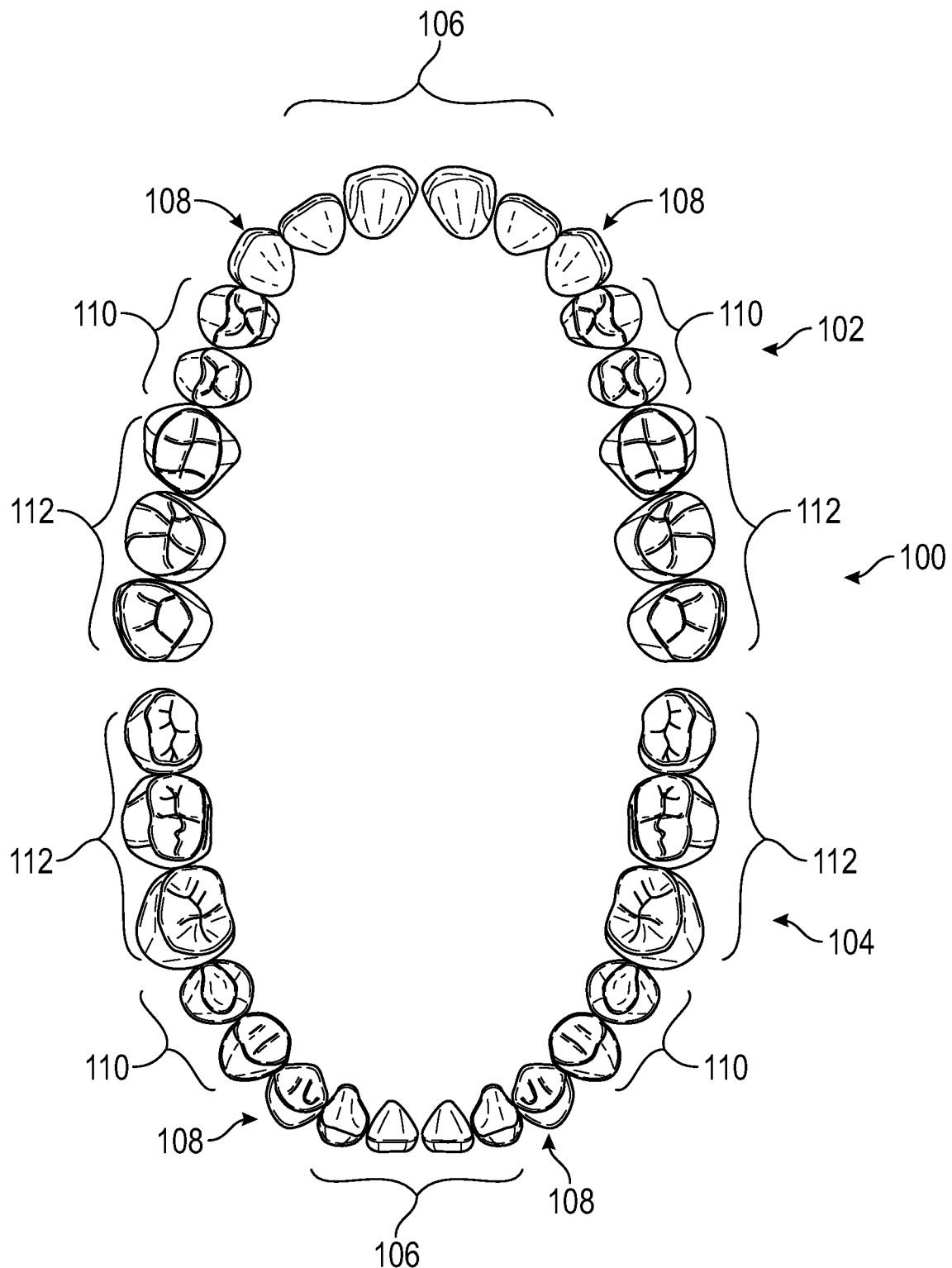
FIG. 1 illustrates a patient's teeth, including the upper and lower dental arches.

Malocclusion of the teeth may be treated using orthodontic brackets and archforms to move the patient's teeth using non-sliding mechanics. For example, scans of a patient's teeth can be taken and a digital model of the patient's teeth can be created, at least in part, from the scans. The teeth of the digital model can be moved from positions of malocclusion (e.g., first positions) to second positions, which may be a final expected alignment of the teeth. Digital brackets can be placed, respectively, on the lingual or buccal surfaces of the teeth in the digital model. In some variants, the digital brackets can be placed before moving the teeth of the digital model from the positions of malocclusion (e.g., first positions) to the second positions.

A physical fixture can be created (e.g., 3D printed, machined, and/or otherwise formed) based on the digital model with the teeth in the second positions and the digital brackets placed. The physical fixture can include retention features (e.g., hooks, slots, locks, holders, etc.) that can retain portions of an archform such as bracket connectors. The retention features can be positioned based on the corresponding positioning of the digital brackets in the digital model with the teeth in the second positions, such that the relative positioning of the retention features to each other is the same as or similar to the relative positioning of the digital brackets to each other in the digital model. In some variants, the physical fixture can be a physical model of the patient's teeth corresponding to the digital model of the patient's teeth in the second positions and the retention features positioned on the teeth of the physical model can be based on the corresponding positioning of the digital brackets in the digital model.

An archform, which may also be referred to as an archwire, can be made of a shape memory material, such as nickel-titanium alloy (e.g., Nitinol). The archform can be cut (e.g., laser, waterjet, etc.) from a sheet of material (e.g., shape memory material). The archform can include bracket connectors that can be coupled to brackets and interproximal segments, such as interproximal loops, that can be configured to move one or more teeth of the patient. When cut from the sheet of material, the archform can have a substantially flat two-dimensional shape. The archform can be deflected and coupled to the physical fixture to assume a custom nonplanar shape. Specifically, the bracket connectors of the archform can be coupled to the retention features of the physical fixture. While retained in the custom nonplanar shape, the archform can be set, which can accomplished via exposure to heat. Setting the archform can set a new default or memorized position for the archform such that the archform is biased toward the memorized custom nonplanar shape when deflected therefrom. Accordingly, if the archform is deflected from the memorized custom nonplanar shape, the archform can exert forces to return the archform back toward the memorized custom nonplanar shape.

An indirect bonding (IDB) tray can be formed based on the digital model. The teeth of the digital model, with the digital brackets disposed thereon, can be returned back to the positions of malocclusion that can reflect the current positions of the patient's teeth. In some variants, the IDB tray can be formed based on the digital model with digital brackets placed on the maloccluded teeth of the digital model prior to movement of the teeth to the second positions. An IDB tray can be 3D printed based on the digital model and/or over molded on a physical model of the patient's teeth. The IDB tray can be sized and shaped to fit over the teeth of the patient. The IDB tray can include wells (e.g., pockets, recesses, etc.) that can house orthodontic brackets therein. The wells can be positioned based on the corresponding positioning of the digital brackets in the digital model.

Orthodontic brackets can be placed in respective wells of the IDB tray with contact surfaces (e.g., bonding surfaces) exposed. An adhesive can be applied to the contact surfaces and the loaded IDB tray can be placed over the teeth of the patient, positioning the orthodontic brackets at locations on the teeth of the patient that correspond to the positioning of the digital brackets on the teeth in the digital model. The orthodontic brackets can bond to the teeth of the patient, which can be facilitated by exposing the adhesive to light (e.g., UV light), heat, low temperatures, and/or chemical(s).

As described herein, it can be difficult to determine a quantity of adhesive that is suitable for bonding an orthodontic bracket to a patient's tooth. If too much adhesive is used, a clinician may need to clean up excess adhesive post bonding, which can waste adhesive and extend the length of a patient's chair time. If too little adhesive is used, a weak bond may be formed between the orthodontic bracket and the patient's tooth, which may result in the orthodontic bracket inadvertently debonding from the tooth.

With the orthodontic brackets bonded to the teeth of the patient, the archform can be deflected from the memorized custom nonplanar shape and coupled to the bonded orthodontic brackets. The bracket connectors of the archform can be coupled, e.g., locked, to the bonded orthodontic brackets such that the archform does not slide with respect to the brackets. As described, the deflected archform can exert forces on the teeth of the patient as the archform exerts forces to move toward the undeflected position (e.g., memorized custom nonplanar shape), which can move the teeth of the patient, using non-sliding mechanics, toward seconds positions that correspond to the second positions of the teeth in the digital model (e.g., final alignment of the teeth).

In some variants, a series of archforms can be sequentially installed in the patient's mouth (e.g., coupled to the brackets) and then replaced to move the patient's teeth from positions of malocclusion to second positions. For example, an initial archform set in the custom nonplanar shape may be used for an initial stage of treatment for initially moving the teeth of the patient toward the second positions. An intermediate archform set in the custom nonplanar shape, which may be stiffer than the initial archform, may be used for an intermediate stage of treatment for moving the teeth of the patient closer toward the second positions. A final archform set in the custom nonplanar shape, which may be stiffer than the intermediate archform, may be used for a final stage of treatment for moving the teeth of the patient closer toward or to the second positions.

FIG. 1 illustrates teeth 100 of a patient, including the upper dental arch 102 and the lower dental arch 104. The human mouth includes a variety of teeth, including incisors 106, canines 108, premolars 110, and molars 112. Each of the foregoing varieties can have different characteristics, sizes, shapes, contours, and/or purposes. For example, incisors 106 are typically smaller than molars and are used to bit into and tear food, while molars 112 include large and relatively flat biting surfaces to crush and grind food. Furthermore, the same variety of teeth can vary depending on whether positioned on the upper dental arch 102 or lower dental arch 104. For example, the upper incisors 106 are typically larger than lower incisors 106. Furthermore, the same tooth can have different characteristics, sizes, shapes, contours, and/or purposes from person to person. Accordingly, in some instances, a variety of brackets with different characteristics, such as size, may be bonded to the surfaces of the teeth of a patient to accommodate different teeth within the patient's mouth.

Figure 2A:
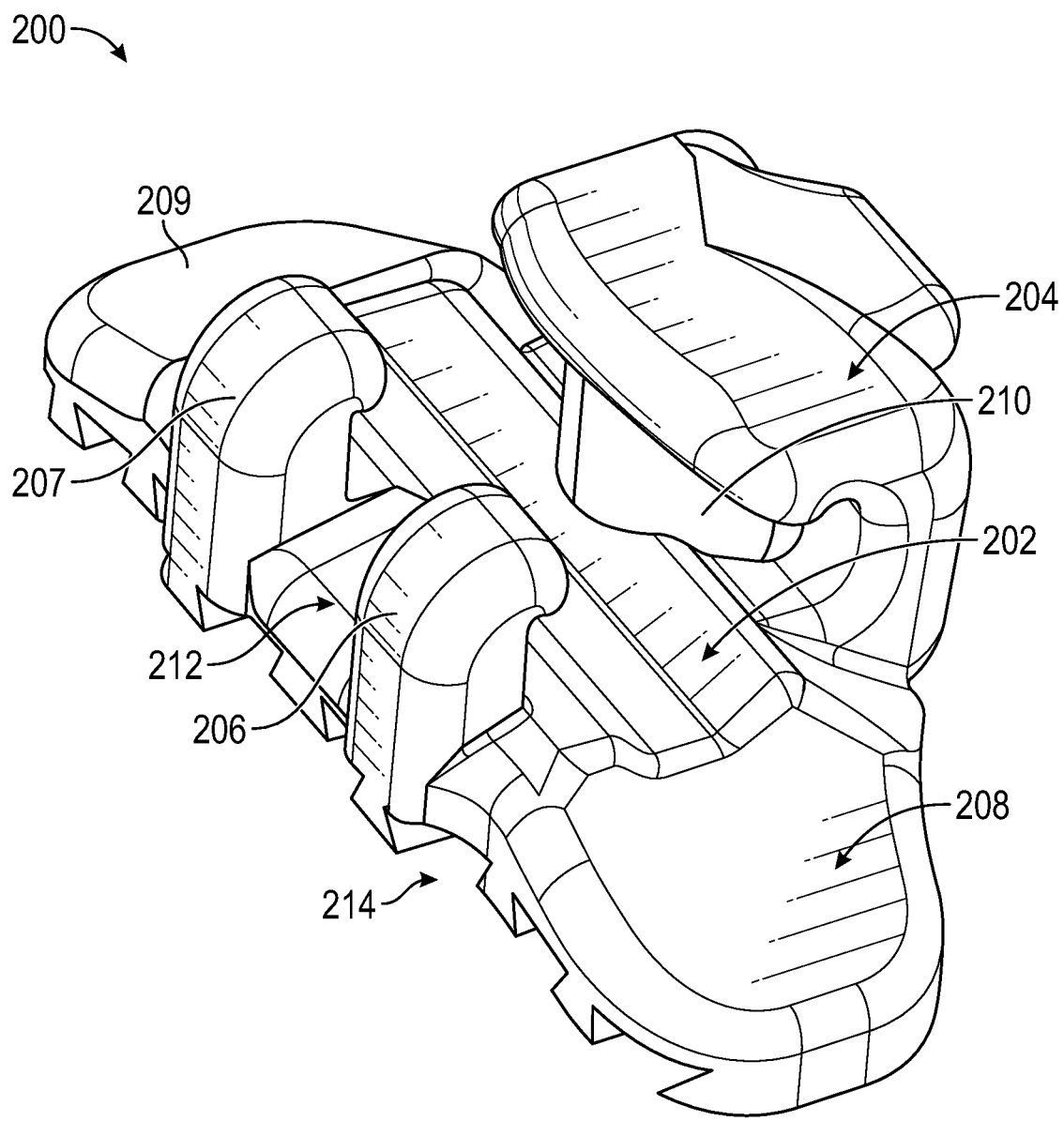
FIGS. 2A and 2B illustrate views of an orthodontic bracket.
Figure 2B:
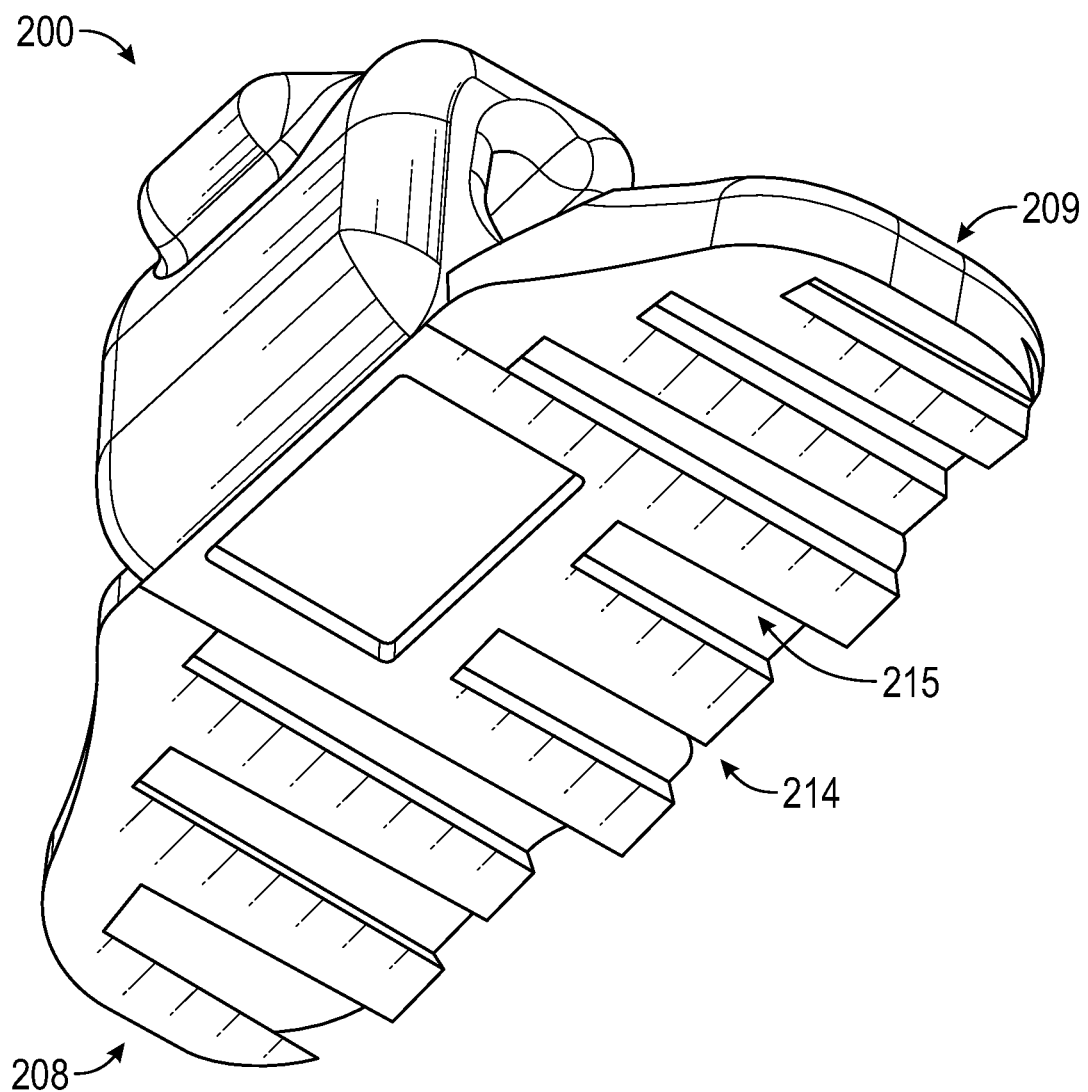

For example, FIGS. 2A and 2B illustrate a bracket 200, which may be at least used on molars 112. As shown, the bracket 200 can include lateral extensions or wings 208, 209 that extend in the medial-distal direction when the bracket 200 is bonded to a tooth. The relatively larger size of molars 112 may permit the incorporation of lateral extensions 208, 209. The lateral extensions 208, 209 can facilitate increased control (e.g., rotational) of a molar 112. The bracket 200 can include a contact or bonding surface 214 that is configured to be bonded to the surface of a tooth of the patient. The contact surface 214 can include contours or grooves 215, which can increase surface area of the contact surface 214 to improve bonding between the bracket 200 and the surface of the tooth with adhesive. As illustrated, the lateral extensions 208, 209 increase the size of the contact surface 214, which can further increase the strength of the bond between the bracket 200 and the surface of the tooth.

The bracket 200 can include a variety of features that facilitate coupling to an archform. The bracket 200 can include a slot 202, which can be disposed between a retainer 204 and stops 206, 207. The slot 202 can receive a bracket connector of an archform therein such that the archform does not slide with respect to the bracket 200. The retainer 204 and the stops 206, 207 can at least prevent movement of the bracket connector relative to the bracket 200 in the gingival-occlusal direction. The bracket 200 can include a spring 210 (e.g., C-spring) that can lock the bracket connector within the slot 202. The spring 210 can be disposed in the retainer 204 and push the bracket connector against the stops 206, 207 to lock the bracket connector within the slot 202. A gap 212 can space apart the stops 206, 207 and receive a portion of the bracket connector therein such that the stops 206, 207 impede medial-distal movement of the bracket connector relative to the bracket 200.

Figure 3A:
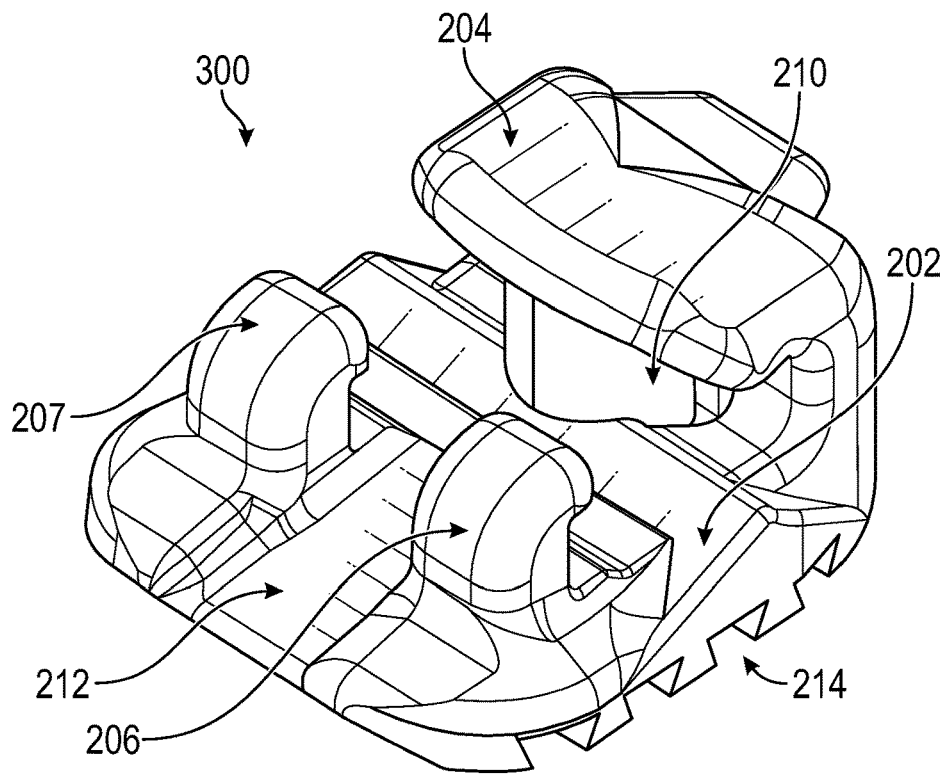
FIGS. 3A and 3B illustrate views of another orthodontic bracket.
Figure 3B:
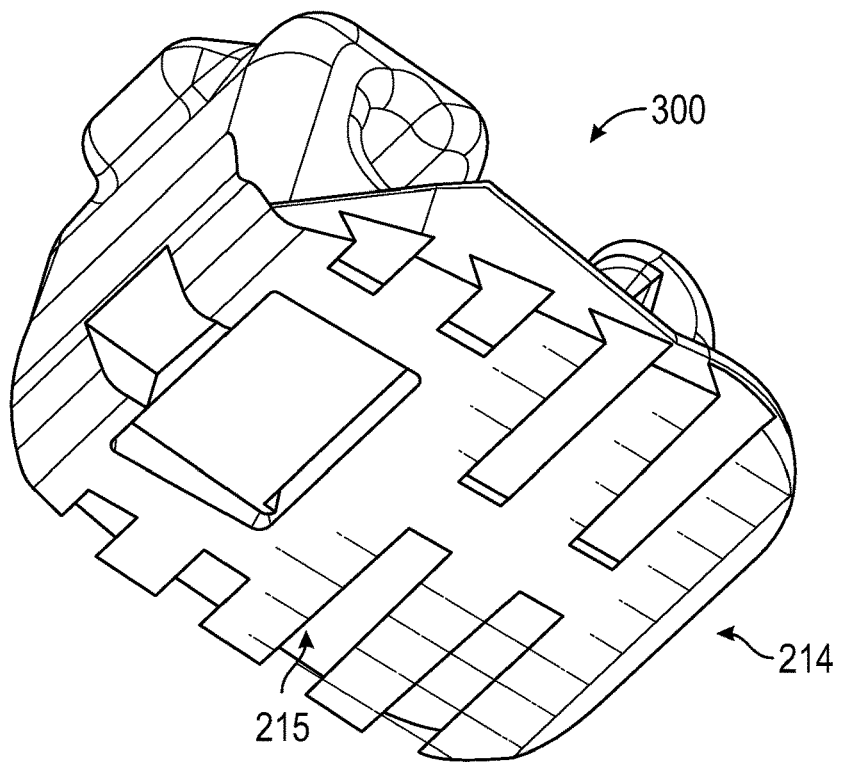

FIGS. 3A and 3B illustrate a bracket 300, which may be used at least on premolars 110, canines 108, and/or incisors 106. As shown, the bracket 300 omits the lateral extensions illustrated in FIGS. 2A and 2B, which can at least be attributed to the smaller size of the premolars 110, canines 108, and/or incisors 106 compared to the molars 112. Without the lateral extensions, the contact or bonding surface 214 of the bracket 300 is smaller than the contact or bonding surface 214 of the bracket 200. Additionally, the contours 215 in the contact surface 214 of the bracket 300 may be different than the those of the bracket 200. At least these differences in bracket size and characteristics can change the quantity of adhesive used to bond the brackets to the surface of the teeth. For example, a quantity of adhesive used to bond the bracket 200 to a molar 112 may be larger than a quantity of adhesive used to bond the bracket 300 to a premolar 110, canine 108, and/or incisor 106.

The bracket 300 can include similar features to retain a portion of the archform (e.g., the bracket connector). The bracket 300 can at least include a slot 202, retainer 204, stops 206, 207, gap 212 disposed between the stops 206, 207, and/or spring 210 as described in reference to the bracket 200.

Figure 4:
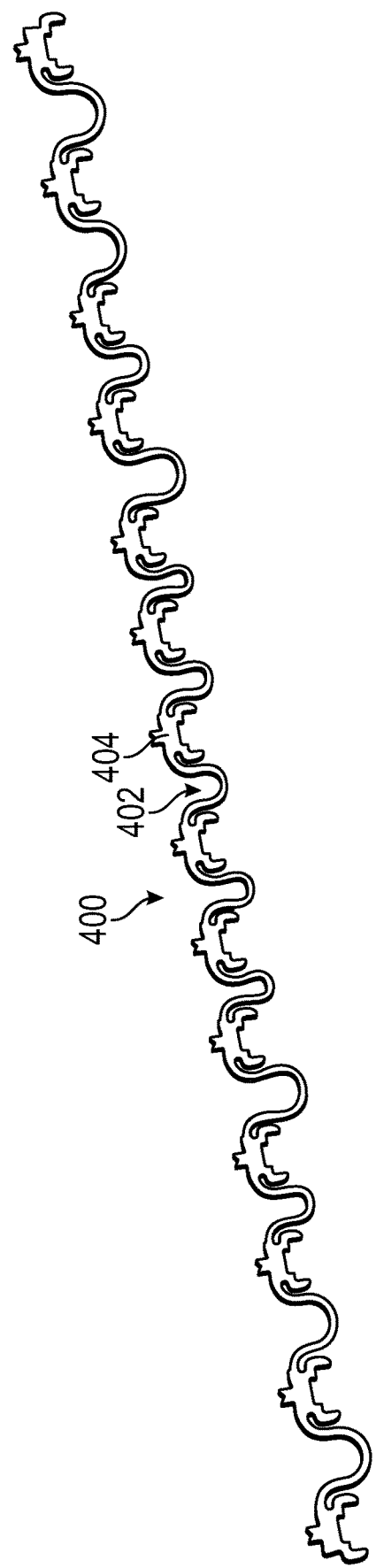
FIG. 4 illustrates an archform.

FIG. 4 illustrates an archform 400, which can also be referred to as an archwire. The archform 400 can have a rectangular cross-section. The archform 400, as described herein, can be cut from a sheet of material, such as shape memory material (e.g., nickel titanium). The archform 400 can include a plurality of bracket connectors 404 that can be coupled to orthodontic brackets to install the archform 400 in the mouth of a patient. The archform 400 can include a plurality of interproximal segments 402. The interproximal segments 402 can be disposed between adjacent bracket connectors 404. The interproximal segment 402 can include loops. The loops can extend in a gingival direction when the archform 400 is installed in the mouth, which can improve aesthetics and/or facilitate flossing. The loops can open to move adjacent teeth apart from each other. The loops can close to move adjacent teeth closer together.

As shown, the archform 400 is in a two-dimensional shape. As described herein, the archform 400 can be set in a custom nonplanar shape using a fixture based on a digital model of a patient's teeth in second positions, which may be a final alignment of the teeth. The archform 400 can be held in the custom nonplanar shape by the fixture and set by exposure to heat such that the custom nonplanar shape is the default or memorized position of the archform 400. The archform 400 can follow the entire upper or lower dental arch of a patient or a segment thereof.

Figure 5:
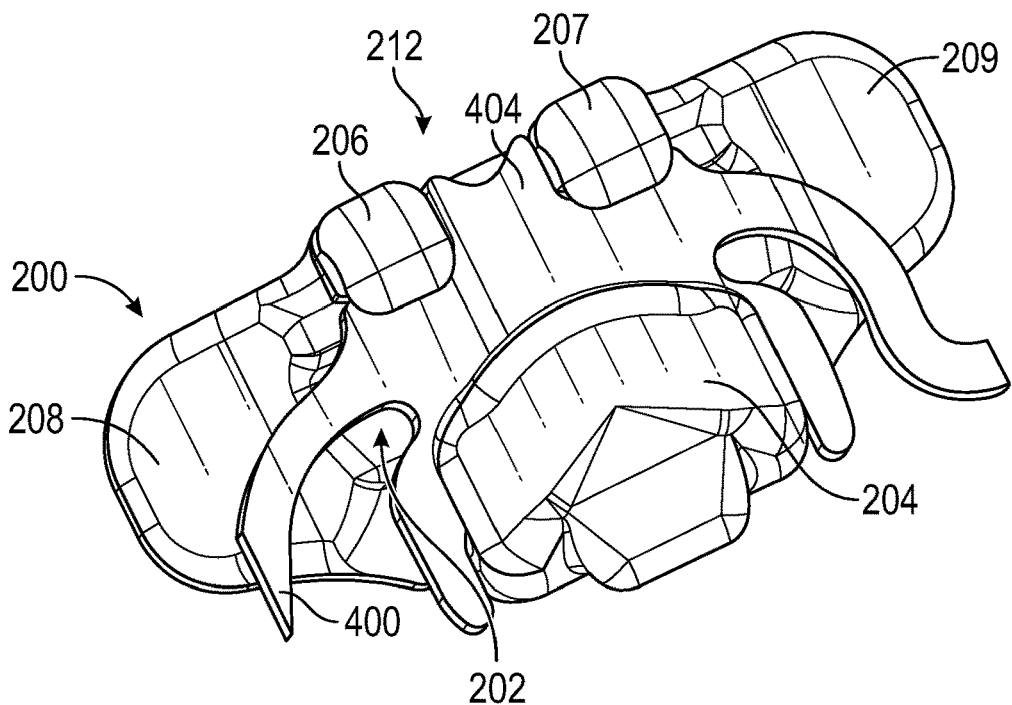
FIG. 5 illustrates the bracket of FIGS. 2A and 2B with a bracket connector of an archform coupled to the bracket.

FIG. 5 illustrates the bracket connector 404 coupled with the bracket 200 such that the bracket connector 404 will not slide with respect to the bracket 200. The bracket connector 404 is disposed within the slot 202 of the bracket 200. The stops 206, 207 and retainer 204 cooperate to retain the bracket connector 404 within the slot and prevent movement of the bracket connector 404 in the occlusal-gingival direction. A portion of the bracket connector 404, e.g., the tongue or tab, can be disposed in the gap 212 between the stops 206, 207 which can help impede the bracket connector 404 from sliding relative to the bracket 200 in the medial-distal direction. As described herein, the spring 210 can push the bracket connector 404 against the stops 206, 207 locking the bracket connector 404 within the bracket 200. In some variants, the bracket connector 404 may be tied to the bracket 200.

Figure 6:
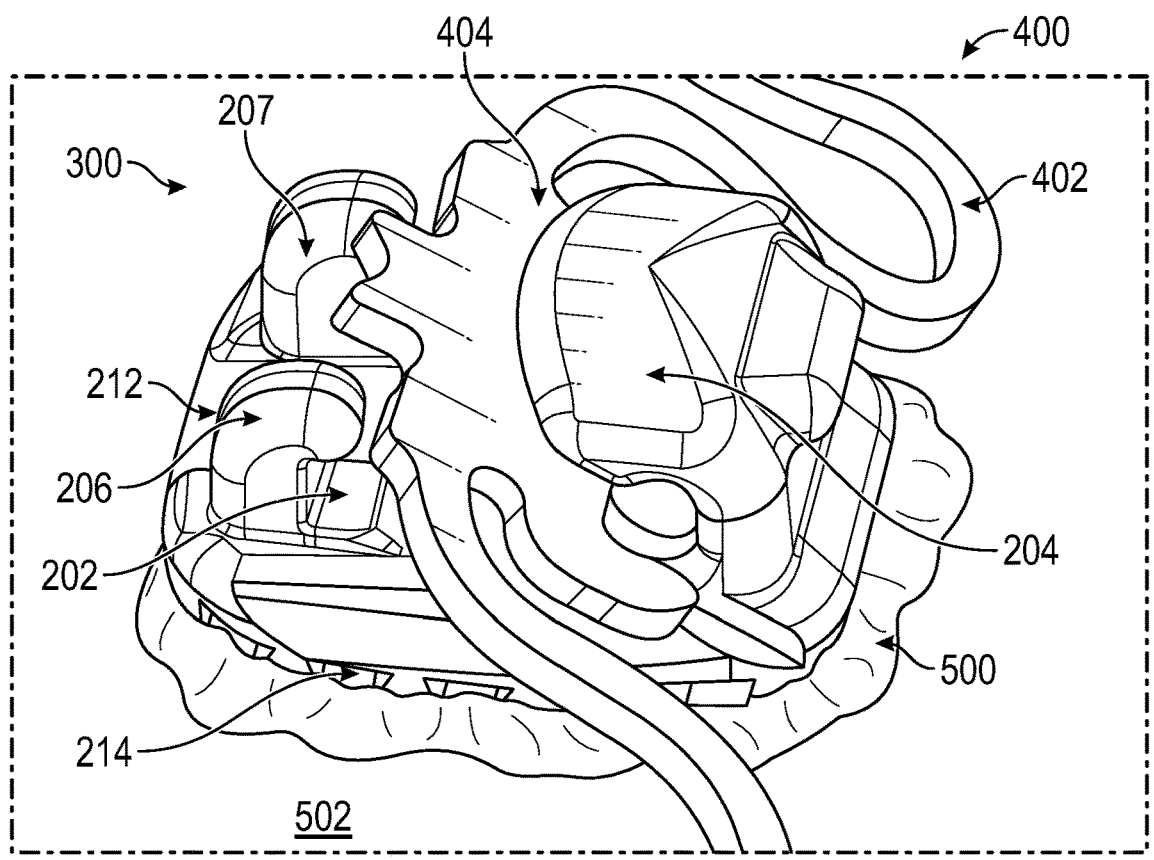
FIG. 6 illustrates the bracket of FIGS. 3A and 3B bonded to the surface of a tooth and receiving a bracket connector of an archform.

FIG. 6 shows the bracket 300 bonded to a tooth surface 502 with a bonding agent or adhesive 500. The adhesive 500 can, in some variants, cure from exposure to air. In some variants, the adhesive 500 can cure from exposure to light, such as UV light. In some variants, the bracket 300 with adhesive applied to the contact surface 214 can be disposed on the tooth surface 502 and, after placement, the adhesive 500 can be exposed to UV light until the adhesive 500 is cured or substantially cured. As shown, the adhesive 500 is extending beyond a periphery of the contact surface 214 which, in some instances, may be removed post bonding. In some variants, an amount of adhesive 500 can be applied to the contact surface 214 for bonding such that the adhesive 500 does not substantially extend beyond a periphery of the contact surface 214 after placement on the tooth surface 502. As shown, the bracket connector 404 is being installed into the slot 202 of the bracket 300.

FIG. 7 illustrates an example method 700 of determining a quantity of adhesive to bond a bracket to a tooth surface. This flow diagram is provided for the purpose of facilitating description of aspects of some embodiments. The diagram does not attempt to illustrate all aspects of the disclosure and should not be considered limiting.

At block 702, a scan (e.g., 3D scans and/or 2D scans) can be taken of the inside of the patient's mouth (e.g., dental arches). The scan can capture data regarding the type, size, shape, contours, surface features, and/or other characteristics of the patient's teeth. The scans can be taken by the patient, caretaker of the patient, and/or clinician. The scan can be performed using a camera and/or sensor of a computer, device connected to a computer, and/or a mobile device, such as a smartphone. In some variants, an application can be used to perform the scans—providing the patient with instructions on how to perform the scan and when a scan is successful. The scan can be performed using the mobile device's built-in camera or via an attachment that operatively connects to the mobile device or computer. In some variants, the scan can be captured using a digital intra-oral scanner and/or a cone-beam computed tomography (CBCT) X-ray scanner. The scanned data can be sent to a manufacturer of orthodontic appliances for processing and/or use.

At block 704, a digital model of the patient's teeth in first positions can be created based on scans of the inside of the patient's mouth. The first positions can correspond to the current positions of the patient's teeth which can be maloccluded positions. The digital model can represent the unique size, shape, contours, surface features, and/or other characteristics of the patient's teeth. The digital model can be displayed to an operator for viewing and/or manipulation. In some variants, the digital model can be automatically generated by software implemented on a computing device using the scans of the inside of the patient's mouth.

At block 706, a digital bracket suitable for bonding on a surface of a tooth can be selected from a variety of digital brackets. As discussed herein, certain types of brackets may be more suitable and/or preferred for bonding on a given tooth but not others. For example, a bracket with lateral extensions may be suitable for bonding on the molars but not on the lower incisors 106 because of differences in size and shape. In some variants, an operator can select a bracket from a variety of brackets for placement on a tooth based on the type of tooth and/or features of the tooth shown in the digital model. In some variants, software implemented on a computing device may suggest one or more brackets from a variety of brackets for placement on a tooth based on the type of tooth and/or features of the relevant tooth. In some variants, software implemented on a computing device may select a bracket from a variety of brackets based on the type of tooth and/or features of the relevant tooth.

At block 708, the selected digital bracket can be digitally placed on the surface of the relevant tooth of the digital model. In some variants, the operator can place the selected digital bracket on the surface (e.g., lingual or buccal surface) of the tooth in the digital model. In some variants, the selected digital bracket can be automatically placed on the surface of the tooth in the digital model. The processes described in reference to block 706 and block 708 can be repeated to select and respectively place a plurality of digital orthodontic brackets on surfaces of the teeth in the digital model, which can include every tooth of the digital model or only some of the teeth of the digital model.

At block 710, a quantity (e.g., volume) of adhesive can be determined to bond a contact surface of a bracket corresponding to the selected digital bracket to a respective surface of a tooth of the patient corresponding to the tooth of the digital model. The determination of the quantity of adhesive can at least be based on the known geometry of the contact surface of the bracket and the geometry of the respective surface of the tooth (using data regarding the type, size, shape, contours, surface features, and/or other characteristics from the scan and/or digital model of the patient's teeth) at the location the bracket will be placed, which can be based on the digital model. As described herein, a variety of orthodontic brackets can be used that have contact surfaces of varying geometry, e.g., sizes, shapes, etc., which can be known by a computing device having one or more processors, memory, instructions, a communication interface, a display, controllers, a user interface, and/or other features requisite to determine the quantity of adhesive to perform a bond. As more orthodontic brackets are developed, data indicative of the geometry of the bracket, including the contact surface, can be stored in the memory of the computing device. In some variants, new orthodontic brackets can be scanned, and the scanned data, indicative of the geometry of the bracket, including the contact surface, can be stored in the memory of the computing device. As described herein, based on the known geometry of the bracket and the scan data and/or digital model of the patient's teeth, the computing device can determine a quantity of adhesive to bond the selected orthodontic bracket at a specific location on the patient's teeth using an algorithm. The quantity of adhesive can change based on the type of bracket selected, type of tooth that the bracket will be bonded to, the unique characteristics of the tooth that the bracket will be bonded to, the location on the tooth that the bracket will be bonded to, the type of adhesive, and/or others.

Figure 8:
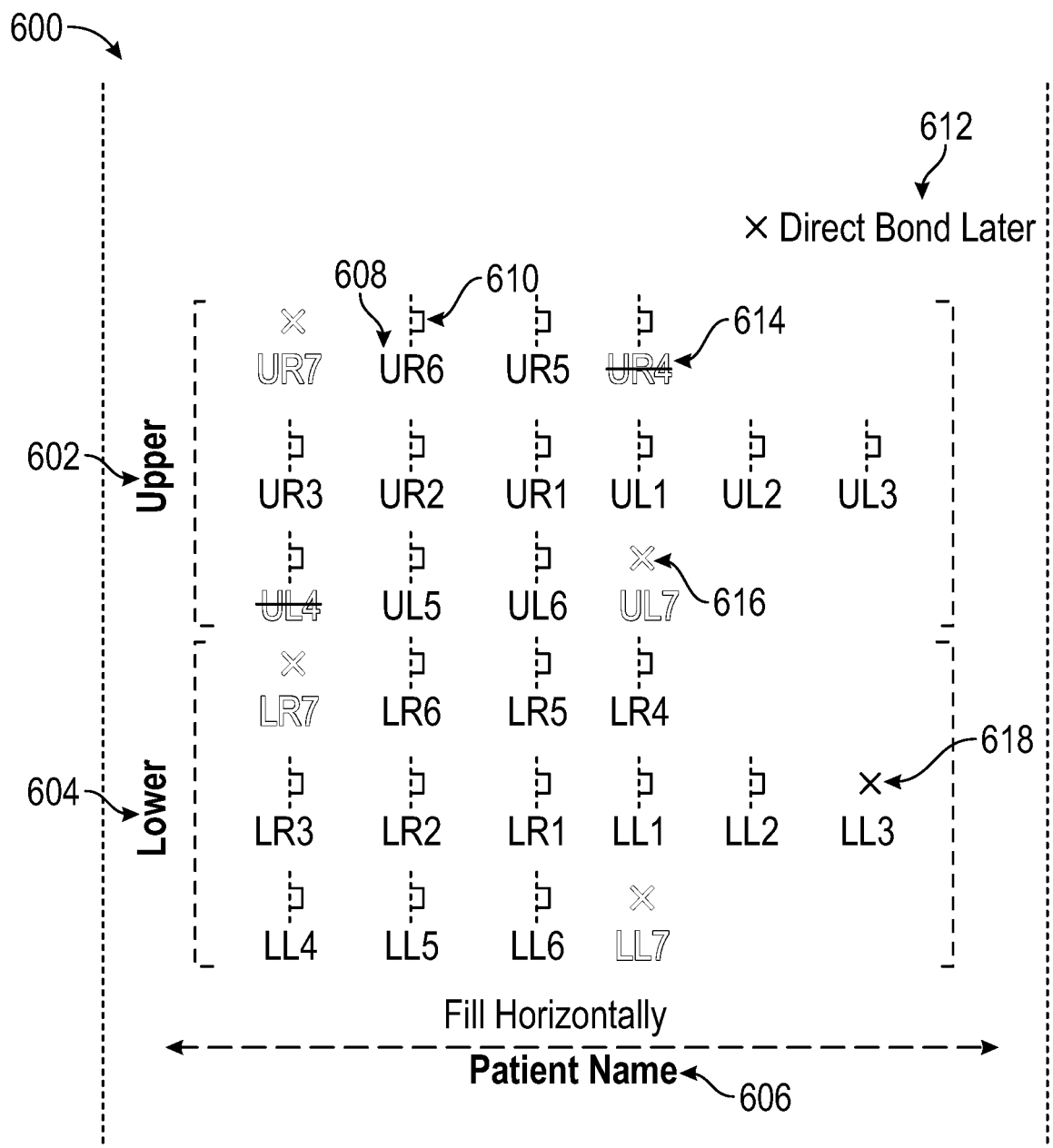
FIG. 8 illustrates an instruction guide that graphically represents at scale a quantity of adhesive to bond a selected bracket to a specific tooth.

FIG. 8 illustrates an instruction guide 600 (e.g., graphic, instruction card, etc.) that can be used to instruct a clinician or operator as to the quantity (e.g., volume) of adhesive to apply to a contact surface of a orthodontic bracket to bond a specific bracket on a specific tooth at a specific location. In some variants, the instruction guide 600 can be printed onto a sheet of material, such as paper. In some variants, the instruction guide 600 can be included in a kit that is specific to a patient. The instruction guide 600 can include a patient identifier 606 to pair the instruction guide 600 with the patient. The kit can include a plurality of orthodontic brackets, an IDB tray, one or more archforms, an installation tool, adhesive, primer, and/or other components or features described herein. In some variants, the instruction guide 600 can be displayed on a screen. The instruction guide 600 can include at least two sections for organization, which can include the upper section 602 that corresponds to the teeth of the upper arch of a patient and the lower section 604 that corresponds to the teeth of the lower arch of the patient. All or some of the teeth of the patient can respectively correspond to a tooth identifier 608 (e.g., UR6, UR5, LR5, LR1, LL1, etc.) on the instruction guide 600 that can be positioned in the upper section 602 or lower section 604.

An adhesive quantity graphic 610 can be juxtaposed a corresponding tooth identifier 608. The adhesive quantity graphic 610 can visually indicate, at scale, a quantity (e.g., volume) of adhesive, which can be determined based on method 700, that should be applied to a corresponding orthodontic bracket to be used to bond the bracket at a specific location on a surface of the tooth corresponding to the tooth identifier 608. The adhesive can be stored in a syringe, container, squeeze container, tube, squeeze tube, and/or other device with a dispenser opening of a known size such that the volume of adhesive dispensed from the syringe is a product of the size of the dispenser opening multiplied by the length of the dispensed adhesive. The width of the adhesive quantity graphic 610 can be the same as the width (e.g., diameter) of the opening of the syringe or other device. Accordingly, a computing device can determine a quantity (e.g., volume) of adhesive to bond the selected bracket to the surface of the tooth at a specific location on the tooth, as described herein, and create an adhesive quantity graphic 610 with a width that is the size of the opening of the syringe or other device and a sufficient length to correlate to the determined volume of adhesive to bond the selected bracket to the surface of the tooth at the specific location on the tooth as planned in the digital model. In practice, a clinician can dispense adhesive from the syringe through the dispensing opening until a length (e.g., size) of a side or horizontal profile of the dispensed adhesive visually matches the length of the adhesive quantity graphic 610 to ensure that a suitable amount of adhesive is applied to the contact surface of the selected orthodontic bracket for bonding.

The instruction guide 600 can include a legend 612 that indicates the meaning of certain graphics of the instruction guide 600. The instruction guide 600 can include a direct bond later indicator 618, such as an X mark in an eye-catching color such as green or others, juxtaposed a tooth identifier 608 to indicate that the selected bracket for the corresponding tooth should be direct bonded later rather than bonded up with the use of an IDB tray, as described herein. The instruction guide 600 can include a do-not-treat indicator 616, which can indicate that a tooth is not being treated (e.g., no bracket should be bonded to the tooth). The do-not-bond indicator 616 can include a tooth identifier, which can be greyed out, and a X mark, which can be greyed out. The instruction guide 600 can include struck through tooth identifiers 614, which can indicate that the patient is missing a tooth at that location. The struck through tooth identifiers 614 can be greyed out.

Figure 9:
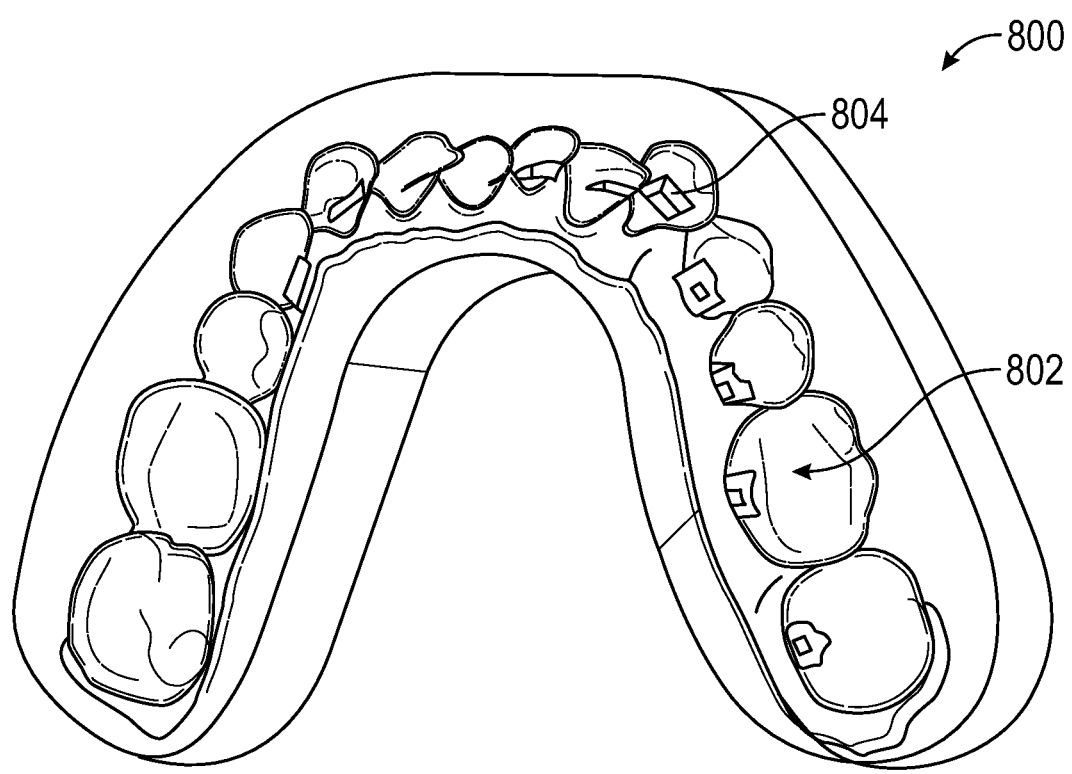
FIG. 9 illustrates an indirect bonding tray.

FIG. 9 illustrates an indirect bonding tray (IDB) tray 800, which can be formed based on the digital model of the patient's teeth with digital brackets disposed thereon. The IDB tray 800 can be used to transfer orthodontic brackets to planned positions, based on the digital model, to the surfaces of the patient's teeth. In some variants, the IDB tray 800 can be used to transfer other orthodontic appliances to the patient's teeth, such as bite turbos, power arms, buttons, archforms, and/or others.

The IDB tray 800 can include cavities 802 configured to receive the teeth of the patient such that the IDB tray 800 can be disposed over the teeth of the patient. The IDB tray 800 can include handles to facilitate handling. The IDB tray 800 can be configured to be placed over an entire dental arch of the patient or a segment thereof. The IDB tray 800 can include wells 804 (e.g., pockets, recesses) sized and shaped to respectively receive orthodontic brackets therein with the contact or bonding surface exposed. The wells 804 can be disposed in the surfaces of the IDB tray 800 forming the cavities 802. The IDB tray 800 can be formed by 3D printing, machining, and/or molding a material over a physical model of the patient's teeth, which may include non-functional brackets or protuberances to form the wells 804. The IDB tray 800 can correspond to an entire dental arch of a patient or a portion of the dental arch of the patient. The IDB tray 800 can be distributed into separate segments (e.g., two, three, four, etc.). In some variants, the IDB tray 800 can be broken up into separate segments (e.g., two, three, four, etc.). In some variants, the IDB tray 800 can include a single cavity corresponding to a single tooth of the patient.

In use, the wells 804 of the IDB tray 800 can be loaded with orthodontic brackets based on the digital model. The IDB tray 800 can include instructional and/or identifying information (e.g., a tooth identifier) to assist an operator or clinician in placing the correct type of bracket in the corresponding well 804 accordingly to the plan of the digital model. The contact or bonding surfaces of the orthodontic brackets can be exposed with the brackets disposed in the wells 804.

With the IDB tray 800 loaded up with orthodontic brackets, a clinician or operator can apply an adhesive to the contact surfaces of the orthodontic brackets. The clinician can use the instruction guide 600 to determine the amount of adhesive to apply to the contact surfaces of each of the orthodontic brackets to avoid using too much or too little adhesive. With the IDB tray 800 loaded up with orthodontic brackets with adhesive applied, the IDB tray 800 can be placed over the teeth of the patient, placing the orthodontic brackets at the planned positions corresponding to the digital brackets on the digital model. The adhesive can cure, bonding the orthodontic brackets to the patient's teeth at the planned positions. The adhesive can be cured with air, heat, low temperatures, and/or light, such as UV light. The archform can be deflected from the custom nonplanar shape and coupled to the orthodontic brackets such that the deflected archform exerts forces on the teeth, causing the teeth to move towards the second positions planned in the digital model.

In some variants, the IDB tray 800 can hold an archform therein. The archform can be deflected from the custom nonplanar shape when held within the IDB tray 800 and, upon placement of the orthodontic brackets in the wells 804, be coupled to the orthodontic brackets such that the orthodontic brackets can be bonded to the patient's teeth with the archform. In some variants, the brackets can be bonded to the tooth and the IDB tray 800 can, after bonding, be used to couple the archform to the orthodontic brackets. In some variants, the IDB tray 800 is soluble in water and/or another fluid, enabling the IDB tray 800 to be dissolved after placing the orthodontic brackets and/or archform on the patient's teeth. In some variants, the IDB tray 800 can transfer orthodontic brackets and an archform to the teeth of the patient at the same time.

FIG. 10 illustrates a method 900 of applying a quantity of adhesive to orthodontic brackets to bond at locations on surfaces of a patient's teeth. This flow diagram is provided for the purpose of facilitating description of aspects of some embodiments. The diagram does not attempt to illustrate all aspects of the disclosure and should not be considered limiting.

At block 902, an IDB tray can be loaded with orthodontic brackets. As described herein, the selected orthodontic brackets can be placed in wells of the IDB tray based on the digital model.

At block 904, adhesive can be dispensed from a syringe, container, squeeze container, tube, squeeze tube, and/or other device such that a side or horizontal profile of the dispensed adhesive matches a size of an adhesive quantity graphic 610 corresponding to a tooth identifier 608 on the instruction guide 600. As described herein, an opening of the syringe or other device can be the same as the width of the adhesive quantity graphic 610 such that the length (e.g., longitudinal length) of the profile of the dispensed adhesive can be compared with the length (e.g., longitudinal length) of the adhesive quantity graphic 610 to verify that a suitable quantity of adhesive has been dispensed for a specific bracket.

At block 906, the dispensed adhesive can be separated from the syringe or other device. In some variants, a thin, composite instrument can be used to cleanly cut the dispensed adhesive at a tip of the syringe or other device.

At block 908, the dispensed adhesive can be transferred to the contact surface of the orthodontic bracket loaded in the IDB tray 800 that is to be placed on a tooth corresponding to the tooth identifier 608 referenced at block 904.

At block 910, the dispensed adhesive can be distributed over the contact surface of the bracket. In some variants, a microbrush can be used to distribute or pad the dispensed adhesive over the contact surface of the bracket for even coverage. The processed described in reference to blocks 904 through 910 can be repeated until the plurality of orthodontic brackets loaded in the IDB tray 800 have adhesive applied therein and are ready for bonding.

At block 912, the IDB tray 800 loaded with orthodontic brackets with adhesive can, optionally, be stored in a light-proof or airtight case that can prevent the curing or at least slow the curing of the adhesive. This can enable an IDB tray 800 to be prepared for bonding before the arrival of a patient, which can decrease the duration of a patient's appointment. In some variants, this can enable the IDB tray 800 to be shipped to a patient or clinic with brackets prepasted with adhesive for more efficient treatment of patients. As described herein, the loaded IDB tray 800 can be positioned over the teeth of the patient to bond the orthodontic brackets at locations. The adhesive can be cured as described herein, and an archform can be deflected and coupled to the bonded brackets to apply forces to the patient's teeth, moving the patient's teeth toward second positions planned in the digital model. As described herein, in some variants, an IDB tray 800 can be used to transfer the archform to couple to the patient's teeth. In some variants, the IDB tray 800 can transfer the archform and brackets to the patient's teeth at the same time.

Reference is made herein to orthodontic appliances and brackets that move teeth using non-sliding mechanics. However, this disclosure should not be limited to non-sliding mechanics. The methods, apparatuses, and/or systems disclosed herein can be applicable to configurations using sliding mechanics (e.g., an archwire that slides relative to brackets). The methods, apparatuses, and/or systems disclosed herein can be applicable to at least any orthodontic treatment plan that involves coupling an archform to the teeth of the patient and/or bonding and/or placing orthodontic brackets on the teeth of the patient. For example, orthodontic brackets formed and cured from an adhesive, as described herein, can be bonded to a patient's teeth and an archform can be coupled thereto that is configured to slide relative to the cured orthodontic bracket to move teeth of the patient. In some variants, bite turbos, power arms, hooks, and/or other features can be formed, cured, and bonded to the patient's teeth according to a treatment plan.

It is intended that the scope of this present invention herein disclosed should not be limited by the particular disclosed embodiments described above. This invention is susceptible to various modifications and alternative forms, and specific examples have been shown in the drawings and are herein described in detail. This invention is not limited to the detailed forms or methods disclosed, but rather covers all equivalents, modifications, and alternatives falling within the scope and spirit of the various embodiments described and the appended claims. Various features of the orthodontic brackets and archforms described herein can be combined to form further embodiments, which are part of this disclosure. The orthodontic brackets described herein can be bonded to a patient's teeth and the archforms described herein can be deflected and coupled thereto as part of a treatment plan. The archforms can move toward a default position and move the patient's teeth from a first position to a second position. The archforms described herein can be installed in sequence to move the patient's teeth. The orthodontic brackets described herein can be bonded to the teeth of the patient in various orientations, which can include orienting the orthodontic bracket in a first gingival-occlusal orientation and reorienting the orthodontic bracket one hundred and eighty degrees to a second gingival-occlusal orientation (e.g., rotating the orthodontic bracket one hundred and eighty degrees).

Methods of using the orthodontic brackets and/or archforms (including device(s), apparatus(es), assembly(ies), structure(s) or the like) are included herein; the methods of use can include using or assembling any one or more of the features disclosed herein to achieve functions and/or features of the system(s) as discussed in this disclosure. Methods of manufacturing the foregoing system(s) are included; the methods of manufacture can include providing, making, connecting, assembling, and/or installing any one or more of the features of the system(s) disclosed herein to achieve functions and/or features of the system(s) as discussed in this disclosure.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "tying a tie onto an orthodontic bracket" includes "instructing the tying of a tie onto an orthodontic bracket." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method comprising: determining, by way of a digital model, a custom quantity of adhesive to bond an orthodontic bracket to a physical tooth at least based on a geometry of a bonding surface of the orthodontic bracket and a geometry of a surface of a digital tooth in the digital model representative of the physical tooth at a location corresponding to a digitally planned placement of the orthodontic bracket; dispensing an adhesive from an opening of a container onto an adhesive quantity graphic on an instructional guide; visually comparing a length of a profile of the dispensed adhesive with a length of the adhesive quantity graphic on the instructional guide, wherein the length of the adhesive quantity graphic is based on the determined custom quantity of adhesive, and wherein a width of the opening of the container and a width of the adhesive quantity graphic are the same; and discontinuing the dispensing of the adhesive from the container when the length of the profile of the dispensed adhesive matches the length of the adhesive quantity graphic on the instructional guide.

2. The method of claim 1, further comprising transferring the dispensed adhesive to the bonding surface of the orthodontic bracket.

3. The method of claim 2, further comprising distributing the dispensed adhesive over the bonding surface of the orthodontic bracket.

4. The method of claim 2, further comprising loading a well of an indirect bonding (IDB) tray with the orthodontic bracket.

5. The method of claim 4, further comprising storing the loaded IDB tray in a light-proof case to prevent the adhesive from curing.

6. The method of claim 4, further comprising placing the loaded IDB tray on the physical tooth to position the orthodontic bracket at the digitally planned placement.

7. The method of claim 6, further comprising exposing the adhesive to UV light to cure the adhesive.

8. The method of claim 1, wherein the container is a syringe.

9. The method of claim 1, further comprising cutting the dispensed adhesive from an end of the container.

10. A kit comprising:
a container comprising an opening providing access into a cavity configured to hold an adhesive therein; and
an instructional guide comprising an adhesive quantity graphic, wherein a length of the adhesive quantity graphic is configured to be visually compared with a length of a profile of adhesive dispensed from the container through the opening onto the adhesive quantity graphic to determine a quantity of dispensed adhesive to be applied to an orthodontic bracket for bonding on a location of a physical tooth of a patient, wherein a width of the opening of the container and a width of the adhesive quantity graphic are the same, and wherein the length of the adhesive quantity graphic corresponds to a custom quantity of adhesive determined, by way of a digital model, to bond the orthodontic bracket to the physical tooth at least based on a geometry of a bonding surface of the orthodontic bracket and a geometry of a surface of a digital tooth in the digital model representative of the physical tooth at a location corresponding to a digitally planned placement of the orthodontic bracket.

11. The kit of claim 10, wherein the adhesive quantity graphic is one of a plurality of adhesive quantity graphics, and the instructional guide further comprising a plurality of tooth identifiers corresponding to respective teeth of the patient, each of the plurality of adhesive quantity graphics being respectively juxtaposed one of the plurality of tooth identifiers to visually indicate a quantity of dispensed adhesive to be applied to the orthodontic bracket corresponding to the tooth identifier.

* * * * *